US012596433B2

(12) United States Patent
Kim et al.

(10) Patent No.: US 12,596,433 B2
(45) Date of Patent: Apr. 7, 2026

(54) WEARABLE DEVICE FOR DETECTING BIOMETRIC INFORMATION OF USER

(71) Applicant: SAMSUNG ELECTRONICS CO., LTD., Suwon-si (KR)

(72) Inventors: Hongki Kim, Suwon-si (KR); Daegyu Kang, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 18/736,119

(22) Filed: Jun. 6, 2024

(65) Prior Publication Data

US 2025/0076982 A1     Mar. 6, 2025

Related U.S. Application Data

(63) Continuation of application No. PCT/KR2024/006922, filed on May 22, 2024.

(30) Foreign Application Priority Data

Sep. 5, 2023   (KR) ........................ 10-2023-0118021
Nov. 21, 2023   (KR) ........................ 10-2023-0162791

(51) Int. Cl.
G06V 40/13        (2022.01)
A61B 5/00         (2006.01)
              (Continued)

(52) U.S. Cl.
CPC ............ G06F 3/014 (2013.01); A61B 5/1172 (2013.01); A61B 5/6826 (2013.01); G06F 3/017 (2013.01);
              (Continued)

(58) Field of Classification Search
CPC ...................................................... G06F 3/048
See application file for complete search history.

(56) References Cited

U.S. PATENT DOCUMENTS 9,880,620 B2    1/2018  Kienzle et al.
12,008,161 B2   6/2024  Nickerson
              (Continued)

FOREIGN PATENT DOCUMENTS

CN          115211647 A     10/2022
KR    10-2016-0016429 A     2/2016
              (Continued)

OTHER PUBLICATIONS

International Search Report (PCT/ISA/210) and Written Opinion (PCT/ISA/237) issued on Sep. 13, 2024 by the International Searching Authority in International Patent Application No. PCT/KR2024/006922.

(Continued)

Primary Examiner — Joseph R Haley
(74) Attorney, Agent, or Firm — Sughrue Mion, PLLC

(57)                    ABSTRACT

According to an embodiment, a wearable device includes a housing including a first surface configured to contact a first body part of a user in a state in which the wearable device is worn on the first body part, a second surface opposite to the first surface, and a groove recessed from the second surface toward the first surface. The wearable device includes a first sensor in the housing disposed toward the groove. The first sensor is configured to detect a second body part of the user, distinct from the first body part of the user, positioned in the groove.

20 Claims, 19 Drawing Sheets

(51) Int. Cl.

| | | |
|---|---|---|
| *A61B 5/1172* | (2016.01) | |
| *G06F 3/01* | (2006.01) | |
| *G06V 40/12* | (2022.01) | |

(52) U.S. Cl.
CPC ...... *G06V 40/1318* (2022.01); *G06V 40/1365* (2022.01)

(56) References Cited

U.S. PATENT DOCUMENTS

| | | | |
|---|---|---|---|
| 2011/0025835 A1 | 2/2011 | Higuchi | |
| 2016/0034742 A1 | 2/2016 | Kim et al. | |
| 2020/0097520 A1* | 3/2020 | Luo ..................... | G06F 9/30036 |
| 2022/0358197 A1* | 11/2022 | Wang ................. | G06V 40/1318 |
| 2023/0297166 A1* | 9/2023 | Martin ................... | G06F 3/014 |
| | | | 345/156 |
| 2024/0029066 A1* | 1/2024 | Tsai ....................... | G06V 40/15 |
| 2024/0126382 A1 | 4/2024 | Yoo | |
| 2024/0156218 A1 | 5/2024 | Min et al. | |

| | | | |
|---|---|---|---|
| 2024/0288938 A1* | 8/2024 | Dahlgren ................ | G06F 3/017 |
| 2024/0411367 A1* | 12/2024 | Kondo ................... | G06F 3/014 |

FOREIGN PATENT DOCUMENTS

| | | |
|---|---|---|
| KR | 10-2016-0096902 A | 8/2016 |
| KR | 10-2017-0055523 A | 5/2017 |
| KR | 10-2017-0091346 A | 8/2017 |
| KR | 10-2018-0066503 A | 6/2018 |
| KR | 10-2018-0102281 A | 9/2018 |
| KR | 10-2020-0004170 A | 1/2020 |
| KR | 10-2022-0100862 A | 7/2022 |
| KR | 10-2464916 B1 | 11/2022 |
| KR | 10-2022-0167978 A | 12/2022 |
| KR | 10-2023-0040048 A | 3/2023 |

OTHER PUBLICATIONS

Communication issued Feb. 18, 2026 by the European Patent Office in European patent Application No. 24862956.0.

* cited by examiner

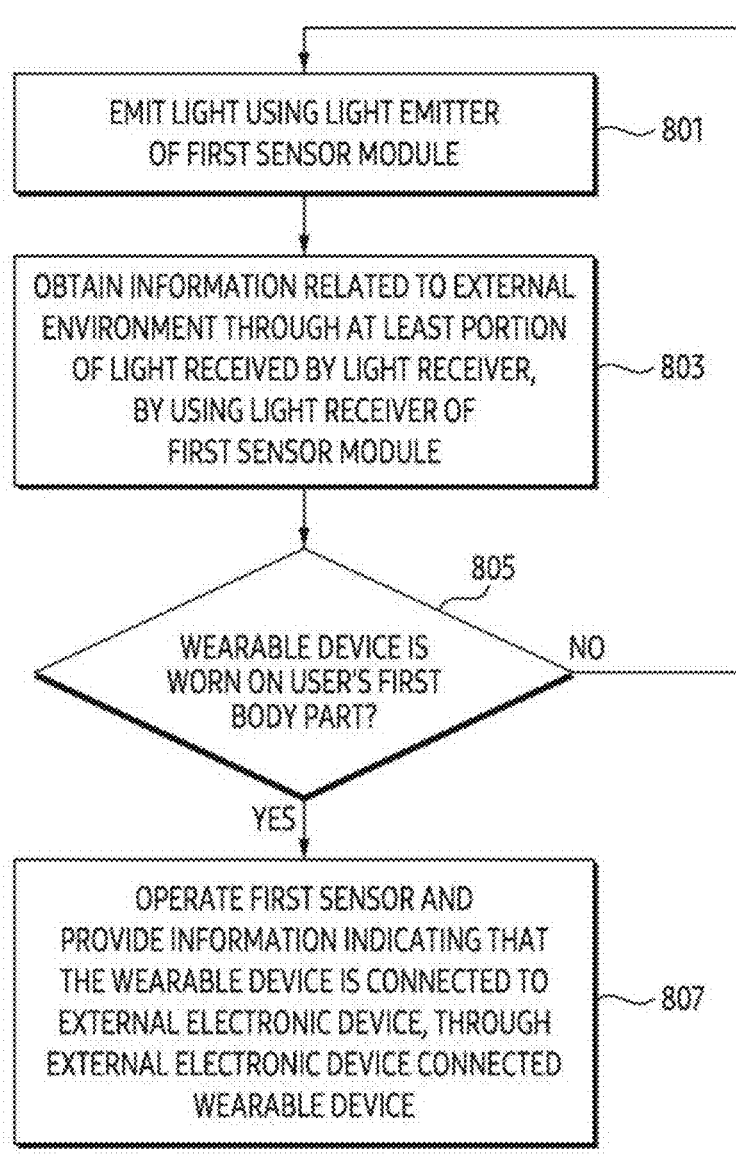

EMIT LIGHT USING LIGHT EMITTER
OF FIRST SENSOR MODULE            ~ 801

OBTAIN INFORMATION RELATED TO EXTERNAL
ENVIRONMENT THROUGH AT LEAST PORTION
OF LIGHT RECEIVED BY LIGHT RECEIVER,            ~ 803
BY USING LIGHT RECEIVER OF
FIRST SENSOR MODULE

805
WEARABLE DEVICE IS
WORN ON USER'S FIRST          NO
BODY PART?

YES

OPERATE FIRST SENSOR AND
PROVIDE INFORMATION INDICATING THAT
THE WEARABLE DEVICE IS CONNECTED TO
EXTERNAL ELECTRONIC DEVICE, THROUGH            ~ 807
EXTERNAL ELECTRONIC DEVICE CONNECTED
WEARABLE DEVICE

FIG. 8A

WEARABLE DEVICE FOR DETECTING BIOMETRIC INFORMATION OF USER

CROSS-REFERENCE TO RELATED APPLICATIONS

This application is a by-pass continuation application of International Application No. PCT/KR2024/006922, filed on May 22, 2024, which is based on and claims priority to Korean Patent Application Nos. 10-2023-0118021, filed on Sep. 5, 2023, and 10-2023-0162791, filed on Nov. 21, 2023, in the Korean Intellectual Property Office, the disclosures of which are incorporated by reference herein their entireties.

BACKGROUND

1. Field

The disclosure relates to a wearable device for detecting biometric information of a user.

2. Description of Related Art

A wearable device may be worn on a part of a user's body. The wearable device may be provided in various types of products. For example, the wearable device may include a ring-shaped device to be worn on a part of the user's body. The wearable device may include various electronic components. The wearable device may include one or more sensors configured to provide information related to the user in order to respond the user's demand.

The above-described information may be provided as a related art for the purpose of helping to understand the present disclosure. No claim or determination is raised as to whether any of the above-described information may be applied as a prior art related to the present disclosure.

SUMMARY

According to an embodiment, a wearable device may comprise a housing including a first surface configured to contact a first body part of a user in a state in which the wearable device is worn on the first body part, a second surface opposite to the first surface, and a groove recessed from the second surface toward the first surface. The wearable device may comprise a first sensor in the housing disposed toward the groove. The first sensor may be configured to detect a second body part of the user, distinct from the first body part of the user, positioned in the groove.

According to an embodiment, a wearable device to be worn on a finger of a user may comprise a housing, having a ring shape, including an inner wall configured to contact a portion of the finger in a state in which the wearable device is worn on the finger, and an outer wall of which a groove is formed on at least a portion. The wearable device may comprise a touch sensor, disposed in the housing, configured to detect a touch on a portion of the groove.

According to an embodiment, a wearable device may comprise a housing including a first surface configured to contact a first body part of a user while the wearable device is worn on the first body part, and a second surface opposite to the first surface. The wearable device may comprise a first sensor module, including a light emitter configured to emit light toward the first surface and a light receiver spaced apart from the light emitter and configured to receive reflected light that is at least a portion of the light emitted by the light emitter and reflected, configured to detect biometric information of the user. The wearable device may comprise a second sensor module, including at least one light emitter, configured to detect a fingerprint of the user using a light emitted from the at least one light emitter, disposed toward the second surface. The wearable device may comprise a hole connected to the second sensor module by extending from the second surface to inside of the housing and at least one cover member disposed on the second sensor module and covering the hole. The wearable device may comprise at least one processor comprising processing circuitry; and memory, comprising one or more storage mediums, storing instructions. The instructions, when executed by the at least one processor individually or collectively, may cause the wearable device to emit light using the light emitter of the first sensor module. The instructions, when executed by the at least one processor individually or collectively, may cause the wearable device to obtain information related to an external environment of the wearable device using the light receiver of the first sensor module through at least a portion of the light received by the light receiver after being emitted from the light emitter.

According to an embodiment, a method of a wearable device may comprise identifying whether the wearable device is worn on a first body part of a user through at least a portion of light received through a light receiver of the wearable device. The method may comprise identifying a second body part of the user, positioned in a groove of the wearable device, through a touch sensor of the wearable device. The method may comprise identifying a motion of the user through a motion sensor of the wearable device, based on identifying the second body part positioned in the groove. The method may comprise identifying whether a first motion among the motion of the user corresponds to a first gesture belonging to a preset gesture group through the motion sensor. The method may comprise receiving information related to a second motion immediately following the first motion through the motion sensor, based on identifying the first motion corresponding to the first gesture. The method may comprise identifying whether the second motion corresponds to a second gesture belonging to the preset gesture group, through the motion sensor, based on receiving the information related to the second motion. The method may comprise performing an event for executing a function corresponding to a combination of the first gesture and the second gesture of an external wearable device through a communication module of the wearable device, based on identifying the second motion corresponding to the second gesture.

According to an embodiment, a non-transitory computer readable storage medium storing one or more programs, the one or more programs may comprise instructions which, when executed by at least one processor of a wearable device with a light receiver, a touch sensor, a groove, a motion sensor, and a communication circuit individually or collectively, cause the wearable device to identify whether the wearable device is worn on a first body part of a user through at least a portion of light received through the light receiver. The one or more programs may comprise instructions which, when executed by the at least one processor individually or collectively, cause the wearable to identify a second body part of the user, positioned in the groove of the wearable device through the touch sensor of the wearable device. The one or more programs may comprise instructions which, when executed by the at least one processor individually or collectively, cause the wearable to identify a motion of the user through the motion sensor of the wearable device based on identifying the second body part positioned in the groove. The one or more programs may comprise instructions which, when executed by the at least one processor individually or collectively, cause the wearable to identify whether a first motion among the motion of the user corresponds to a first gesture belonging to a preset gesture group through the motion sensor. The one or more programs may comprise instructions which, when executed by the at least one processor individually or collectively, cause the wearable to receive information related to a second motion immediately following the first motion through the motion sensor, based on identifying the first motion corresponding to the first gesture. The one or more programs may comprise instructions which, when executed by the at least one processor individually or collectively, cause the wearable to identify whether the second motion corresponds to a second gesture belonging to the preset gesture group through the motion sensor, based on receiving the information related to the second motion. The one or more programs may comprise instructions which, when executed by the at least one processor individually or collectively, cause the wearable to perform an event for executing a function corresponding to a combination of the first gesture and the second gesture of an external electronic device connected to the wearable device through a communication module of the wearable device, based on identifying the second motion corresponding to the second gesture

BRIEF DESCRIPTION OF THE DRAWINGS

The above and other aspects, features, and advantages of certain embodiments of the disclosure will be more apparent from the following description taken in conjunction with the accompanying drawings, in which:

FIGS. 8A and 8B are flowcharts illustrating an operation of a processor of an exemplary wearable device;

DETAILED DESCRIPTIONS

The terms as used in the disclosure are provided to merely describe specific embodiments, not intended to limit the scope of other embodiments. Singular forms include plural referents unless the context clearly dictates otherwise. The terms and words as used herein, including technical or scientific terms, may have the same meanings as generally understood by those skilled in the art. The terms as generally defined in dictionaries may be interpreted as having the same or similar meanings as or to contextual meanings of the relevant art. Unless otherwise defined, the terms should not be interpreted as ideally or excessively formal meanings. Even though a term is defined in the disclosure, the term should not be interpreted as excluding embodiments of the disclosure under circumstances.

The term "couple" and the derivatives thereof refer to any direct or indirect communication between two or more elements, whether or not those elements are in physical contact with each other. The terms "transmit", "receive", and "communicate" as well as the derivatives thereof encompass both direct and indirect communication. The terms "include" and "comprise", and the derivatives thereof refer to inclusion without limitation. The term "or" is an inclusive term meaning "and/or". The phrase "associated with," as well as derivatives thereof, refer to include, be included within, interconnect with, contain, be contained within, connect to or with, couple to or with, be communicable with, cooperate with, interleave, juxtapose, be proximate to, be bound to or with, have, have a property of, have a relationship to or with, or the like. The term "controller" refers to any device, system, or part thereof that controls at least one operation. The functionality associated with any particular controller may be centralized or distributed, whether locally or remotely. The phrase "at least one of," when used with a list of items, means that different combinations of one or more of the listed items may be used, and only one item in the list may be needed.

Figure 1:
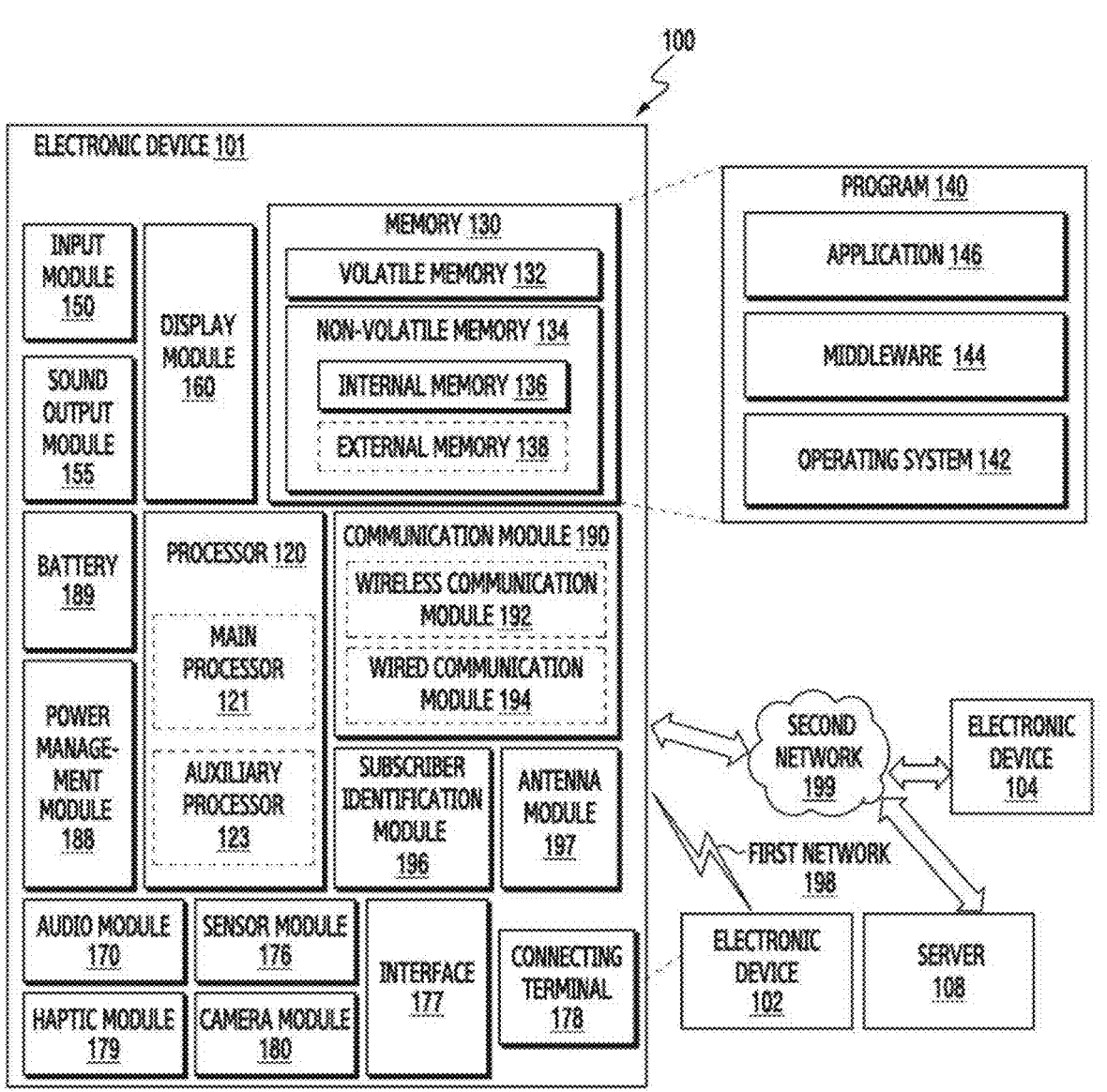
FIG. 1 is a block diagram of an electronic device in a network environment according to an embodiment.

FIG. 1 is a block diagram illustrating an electronic device 101 in a network environment 100 according to various embodiments.

Referring to FIG. 1, the electronic device 101 in the network environment 100 may communicate with an electronic device 102 via a first network 198 (e.g., a short-range wireless communication network), or at least one of an electronic device 104 or a server 108 via a second network 199 (e.g., a long-range wireless communication network). According to an embodiment, the electronic device 101 may communicate with the electronic device 104 via the server 108. According to an embodiment, the electronic device 101 may include a processor 120, memory 130, an input module 150, a sound output module 155, a display module 160, an audio module 170, a sensor module 176, an interface 177, a connecting terminal 178, a haptic module 179, a camera module 180, a power management module 188, a battery 189, a communication module (or communication circuit) 190, a subscriber identification module (SIM) 196, or an antenna module 197. In some embodiments, at least one of the components (e.g., the connecting terminal 178) may be omitted from the electronic device 101, or one or more other components may be added in the electronic device 101. In some embodiments, some of the components (e.g., the sensor module 176, the camera module 180, or the antenna module 197) may be implemented as a single component (e.g., the display module 160).

The processor 120 may execute, for example, software (e.g., a program 140) to control at least one other component (e.g., a hardware or software component) of the electronic device 101 coupled with the processor 120, and may perform various data processing or computation. According to an embodiment, as at least part of the data processing or computation, the processor 120 may store a command or data received from another component (e.g., the sensor module 176 or the communication module 190) in volatile memory 132, process the command or the data stored in the volatile memory 132, and store resulting data in non-volatile memory 134. According to an embodiment, the processor 120 may include a main processor 121 (e.g., a central processing unit (CPU) or an application processor (AP)), or an auxiliary processor 123 (e.g., a graphics processing unit (GPU), a neural processing unit (NPU), an image signal processor (ISP), a sensor hub processor, or a communication processor (CP)) that is operable independently from, or in conjunction with, the main processor 121. For example, when the electronic device 101 includes the main processor 121 and the auxiliary processor 123, the auxiliary processor 123 may be adapted to consume less power than the main processor 121, or to be specific to a specified function. The auxiliary processor 123 may be implemented as separate from, or as part of the main processor 121.

The auxiliary processor 123 may control at least some of functions or states related to at least one component (e.g., the display module 160, the sensor module 176, or the communication module 190) among the components of the electronic device 101, instead of the main processor 121 while the main processor 121 is in an inactive (e.g., sleep) state, or together with the main processor 121 while the main processor 121 is in an active state (e.g., executing an application). According to an embodiment, the auxiliary processor 123 (e.g., an image signal processor or a communication processor) may be implemented as part of another component (e.g., the camera module 180 or the communication module 190) functionally related to the auxiliary processor 123. According to an embodiment, the auxiliary processor 123 (e.g., the neural processing unit) may include a hardware structure specified for artificial intelligence model processing. An artificial intelligence model may be generated by machine learning. Such learning may be performed, e.g., by the electronic device 101 where the artificial intelligence is performed or via a separate server (e.g., the server 108). Learning algorithms may include, but are not limited to, e.g., supervised learning, unsupervised learning, semi-supervised learning, or reinforcement learning. The artificial intelligence model may include a plurality of artificial neural network layers. The artificial neural network may be a deep neural network (DNN), a convolutional neural network (CNN), a recurrent neural network (RNN), a restricted Boltzmann machine (RBM), a deep belief network (DBN), a bidirectional recurrent deep neural network (BRDNN), deep Q-network or a combination of two or more thereof but is not limited thereto. The artificial intelligence model may, additionally or alternatively, include a software structure other than the hardware structure.

The memory 130 may store various data used by at least one component (e.g., the processor 120 or the sensor module 176) of the electronic device 101. The various data may include, for example, software (e.g., the program 140) and input data or output data for a command related thereto. The memory 130 may include the volatile memory 132 or the non-volatile memory 134.

The program 140 may be stored in the memory 130 as software, and may include, for example, an operating system (OS) 142, middleware 144, or an application 146.

The input module 150 may receive a command or data to be used by another component (e.g., the processor 120) of the electronic device 101, from the outside (e.g., a user) of the electronic device 101. The input module 150 may include, for example, a microphone, a mouse, a keyboard, a key (e.g., a button), or a digital pen (e.g., a stylus pen).

The sound output module 155 may output sound signals to the outside of the electronic device 101. The sound output module 155 may include, for example, a speaker or a receiver. The speaker may be used for general purposes, such as playing multimedia or playing record. The receiver may be used for receiving incoming calls. According to an embodiment, the receiver may be implemented as separate from, or as part of the speaker.

The display module 160 may visually provide information to the outside (e.g., a user) of the electronic device 101. The display module 160 may include, for example, a display, a hologram device, or a projector and control circuitry to control a corresponding one of the display, hologram device, and projector. According to an embodiment, the display module 160 may include a touch sensor adapted to detect a touch, or a pressure sensor adapted to measure the intensity of force incurred by the touch.

The audio module 170 may convert a sound into an electrical signal and vice versa. According to an embodiment, the audio module 170 may obtain the sound via the input module 150, or output the sound via the sound output module 155 or a headphone of an external electronic device (e.g., an electronic device 102) directly (e.g., wiredly) or wirelessly coupled with the electronic device 101.

The sensor module 176 may detect an operational state (e.g., power or temperature) of the electronic device 101 or an environmental state (e.g., a state of a user) external to the electronic device 101, and then generate an electrical signal or data value corresponding to the detected state. According to an embodiment, the sensor module 176 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 177 may support one or more specified protocols to be used for the electronic device 101 to be coupled with the external electronic device (e.g., the electronic device 102) directly (e.g., wiredly) or wirelessly. According to an embodiment, the interface 177 may include, for example, a high definition multimedia interface (HDMI), a universal serial bus (USB) interface, a secure digital (SD) card interface, or an audio interface.

A connecting terminal 178 may include a connector via which the electronic device 101 may be physically connected with the external electronic device (e.g., the electronic device 102). According to an embodiment, the connecting terminal 178 may include, for example, a HDMI connector, a USB connector, a SD card connector, or an audio connector (e.g., a headphone connector).

The haptic module 179 may convert an electrical signal into a mechanical stimulus (e.g., a vibration or a movement) or electrical stimulus which may be recognized by a user via his tactile sensation or kinesthetic sensation. According to an embodiment, the haptic module 179 may include, for example, a motor, a piezoelectric element, or an electric stimulator.

The camera module 180 may capture a still image or moving images. According to an embodiment, the camera module 180 may include one or more lenses, image sensors, image signal processors, or flashes.

The power management module 188 may manage power supplied to the electronic device 101. According to an embodiment, the power management module 188 may be implemented as at least part of, for example, a power management integrated circuit (PMIC).

The battery 189 may supply power to at least one component of the electronic device 101. According to an embodiment, the battery 189 may include, for example, a primary cell which is not rechargeable, a secondary cell which is rechargeable, or a fuel cell.

The communication module 190 may support establishing a direct (e.g., wired) communication channel or a wireless communication channel between the electronic device 101 and the external electronic device (e.g., the electronic device 102, the electronic device 104, or the server 108) and performing communication via the established communication channel. The communication module 190 may include one or more communication processors that are operable independently from the processor 120 (e.g., the application processor (AP)) and supports a direct (e.g., wired) communication or a wireless communication. According to an embodiment, the communication module 190 may include a wireless communication module (or wireless communication circuit) 192 (e.g., a cellular communication module or circuit, a short-range wireless communication module or circuit, or a global navigation satellite system (GNSS) communication module or circuit) or a wired communication module 194 (e.g., a local area network (LAN) communication module or a power line communication (PLC) module). A corresponding one of these communication modules may communicate with the external electronic device via the first network 198 (e.g., a short-range communication network, such as Bluetooth™, wireless-fidelity (Wi-Fi) direct, or infrared data association (IrDA)) or the second network 199 (e.g., a long-range communication network, such as a legacy cellular network, a 5G network, a next-generation communication network, the Internet, or a computer network (e.g., LAN or wide area network (WAN)). These various types of communication modules may be implemented as a single component (e.g., a single chip), or may be implemented as multi components (e.g., multi chips) separate from each other. The wireless communication module 192 may identify and authenticate the electronic device 101 in a communication network, such as the first network 198 or the second network 199, using subscriber information (e.g., international mobile subscriber identity (IMSI)) stored in the subscriber identification module 196.

The wireless communication module 192 may support a 5G network, after a 4G network, and next-generation communication technology, e.g., new radio (NR) access technology. The NR access technology may support enhanced mobile broadband (eMBB), massive machine type communications (mMTC), or ultra-reliable and low-latency communications (URLLC). The wireless communication module 192 may support a high-frequency band (e.g., the mmWave band) to achieve, e.g., a high data transmission rate. The wireless communication module 192 may support various technologies for securing performance on a high-frequency band, such as, e.g., beamforming, massive multiple-input and multiple-output (massive MIMO), full dimensional MIMO (FD-MIMO), array antenna, analog beam-forming, or large scale antenna. The wireless communication module 192 may support various requirements specified in the electronic device 101, an external electronic device (e.g., the electronic device 104), or a network system (e.g., the second network 199). According to an embodiment, the wireless communication module 192 may support a peak data rate (e.g., 20 Gbps or more) for implementing eMBB, loss coverage (e.g., 164 dB or less) for implementing mMTC, or U-plane latency (e.g., 0.5 ms or less for each of downlink (DL) and uplink (UL), or a round trip of 1 ms or less) for implementing URLLC.

The antenna module 197 may transmit or receive a signal or power to or from the outside (e.g., the external electronic device) of the electronic device 101. According to an embodiment, the antenna module 197 may include an antenna including a radiating element composed of a conductive material or a conductive pattern formed in or on a substrate (e.g., a printed circuit board (PCB)). According to an embodiment, the antenna module 197 may include a plurality of antennas (e.g., array antennas). In such a case, at least one antenna appropriate for a communication scheme used in the communication network, such as the first network 198 or the second network 199, may be selected, for example, by the communication module 190 (e.g., the wireless communication module 192) from the plurality of antennas. The signal or the power may then be transmitted or received between the communication module 190 and the external electronic device via the selected at least one antenna. According to an embodiment, another component (e.g., a radio frequency integrated circuit (RFIC)) other than the radiating element may be additionally formed as part of the antenna module 197.

According to various embodiments, the antenna module 197 may form an mmWave antenna module. According to an embodiment, the mmWave antenna module may include a printed circuit board, a RFIC disposed on a first surface (e.g., the bottom surface) of the printed circuit board, or adjacent to the first surface and capable of supporting a designated high-frequency band (e.g., the mmWave band), and a plurality of antennas (e.g., array antennas) disposed on a second surface (e.g., the top or a side surface) of the printed circuit board, or adjacent to the second surface and capable of transmitting or receiving signals of the designated high-frequency band.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment, commands or data may be transmitted or received between the electronic device 101 and the external electronic device 104 via the server 108 coupled with the second network 199. Each of the electronic devices 102 or 104 may be a device of a same type as, or a different type, from the electronic device 101. According to an embodiment, all or some of operations to be executed at the electronic device 101 may be executed at one or more of the external electronic devices 102, 104, or the server 108. For example, if the electronic device 101 should perform a function or a service automatically, or in response to a request from a user or another device, the electronic device 101, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 101. The electronic device 101 may provide the outcome, with or without further processing of the outcome, as at least part of a reply to the request. To that end, a cloud computing, distributed computing, mobile edge computing (MEC), or client-server computing technology may be used, for example. The electronic device 101 may provide ultra-low-latency services using, e.g., distributed computing or mobile edge computing. In another embodiment, the external electronic device 104 may include an internet-of-things (IoT) device. The server 108 may be an intelligent server using machine learning and/or a neural network. According to an embodiment, the external electronic device 104 or the server 108 may be included in the second network 199. The electronic device 101 may be applied to intelligent services (e.g., smart home, smart city, smart car, or healthcare) based on 5G communication technology or IoT-related technology.

Figure 2A:
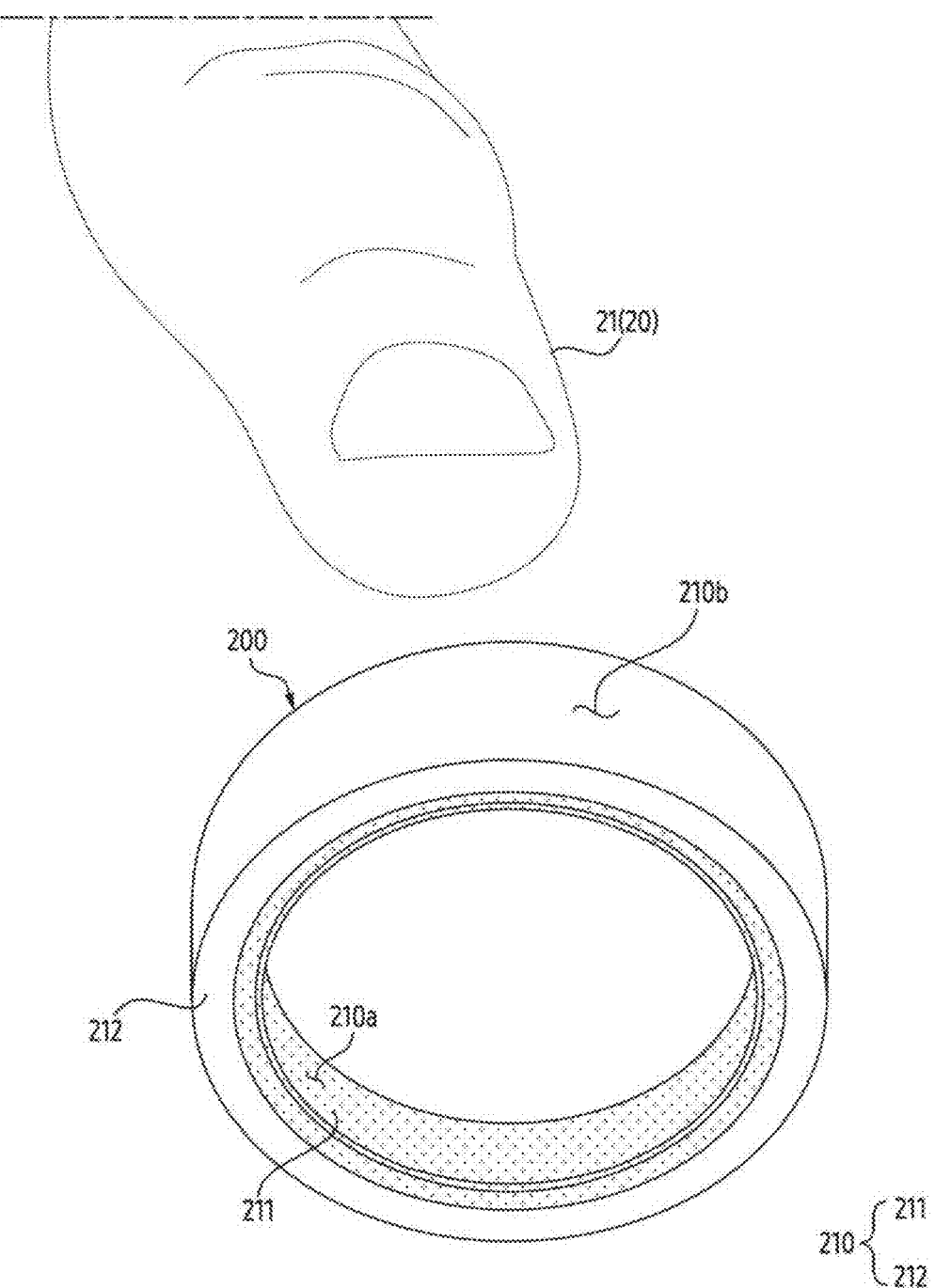
FIG. 2A illustrates an exemplary wearable device.
Figure 2B:
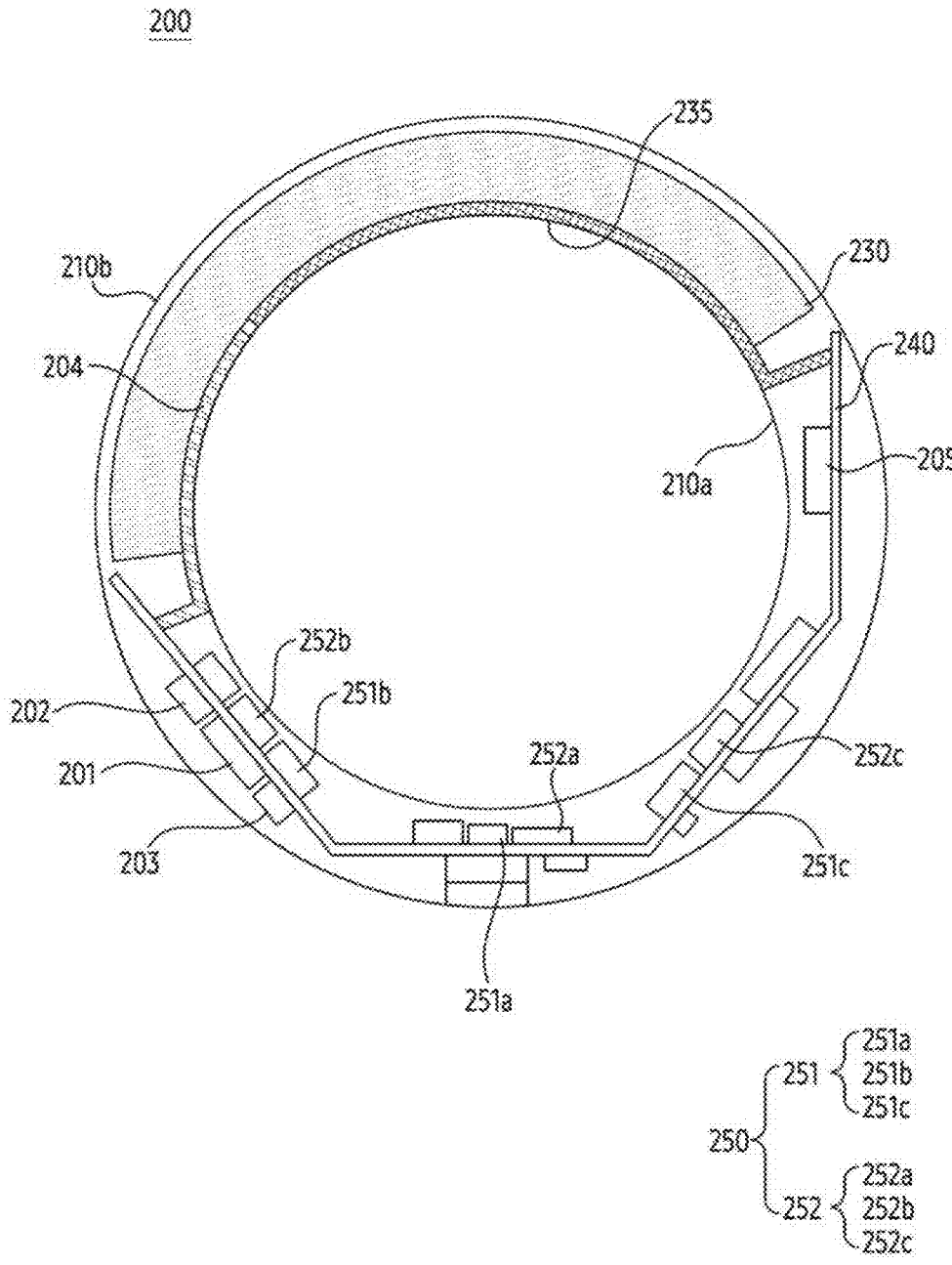
FIG. 2B is a cross-sectional view of an exemplary wearable device.

FIG. 2A illustrates an exemplary wearable device. FIG. 2B is a cross-sectional view of an exemplary wearable device. Referring to FIG. 2A, a wearable device 200 may include a housing 210.

According to an embodiment, the wearable device 200 may be worn on a user. The user may mean a person who wears the wearable device 200. The wearable device 200 may be worn on a part 20 of the user's body. For example, the wearable device 200 may be worn on the part 20 of the user's body. For example, the wearable device 200 may be fastened to the part 20 of the user's body. For example, the wearable device 200 may be detachable with respect to the part 20 of the user's body.

For example, the wearable device 200 may be in contact with the part 20 of the user's body by being worn on the user. For example, the wearable device 200 may be configured to obtain information related to the user through the part 20 of the user's body, by being worn on the user. For example, the wearable device 200 may provide the user with information indicating a state of the user, based on obtaining the information related to the user. For example, the wearable device 200 may provide the information indicating the user's state to the user, by being configured to display the information indicating the user's state through a display of the wearable device 200 and/or an electronic device (e.g., the electronic device 101 of FIG. 1) connected to the wearable device 200. In terms of providing information related to a user wearing the wearable device 200 to the user through the electronic device 101 connected to the wearable device 200, the wearable device 200 may be referred to as the electronic device 102 or the electronic device 104 of FIG. 1, but is not limited thereto.

For example, the part 20 of the user's body where the wearable device 200 is worn may be the user's finger. For example, the housing 210 of the wearable device 200 may have a ring shape in order for the wearable device 200 to be worn on the user's finger. However, it is not limited thereto. The wearable device 200 capable of being referred to as a wearable device may have a shape corresponding to the part 20 of the user's body in order to be worn on the part 20 of the user's body.

According to an embodiment, as shown in FIG. 2A, the housing 210 may include a first surface 210a (of a first frame 211) facing and contacting a first body part 21 of a user while the wearable device 200 is worn on the user's first body part 21, and a second surface 210b (of a second frame 212), which is opposite to the first surface 210a. The first body part 21 may be a finger of the user's fingers. For example, when the wearable device 200 is worn on the user, at least a portion of the first surface 210a may be in contact with the user's first body part 21. For example, the first surface 210a may surround the first body part 21 of the user wearing the wearable device 200. For example, the first surface 210a may cover the first body part 21 of the user wearing the wearable device 200. For example, the first surface 210a may be configured such that the wearable device 200 is fastened to the first body part 21 by pressurizing the user's first body part 21 when the wearable device 200 is worn on the user.

For example, the second surface 210b may form the exterior of the electronic device 101 together with the first surface 210a. For example, the second surface 210b may form a ring-shaped housing 210 together with the first surface 210a. For example, the second surface 210b may be a surface spaced apart from the user's first body part 21 when the electronic device 101 is worn on the user's first body part 21. For example, the first surface 210a may be a surface closest to the user's first body part 21 while the electronic device 101 is worn on the user's first body part 21. The second surface 210b opposite to the first surface 210a may be a surface farthest from the first body part 21. For example, the first surface 210a may be referred to as an inner circumference surface of the housing 210. The second surface 210b opposite to the first surface 210a may be referred to as an outer circumference surface of the housing 210.

Although the wearable device 200 is described as being worn on the user's first body part 21, it is not limited thereto. The first body part 21 is merely used to explain the part 20 of the user's body on which the wearable device 200 is worn, and it should be noted that the body part 20 of the user wearing the wearable device 200 is not limited or arrangement relationship between the body part 20 and the wearable device 200 is not limited. For example, the first body part 21 may be one of the user's fingers, but is not limited thereto.

According to an embodiment, the housing 210 may include the first frame 211 (defining the first surface 210a) and the second frame 212 defining the second surface 210b and coupled to the first frame 211. For example, the first frame 211 may be a portion of the housing 210, which includes the first surface 210a. For example, the first frame 211 may be in contact with the part 20 of the user's body when the wearable device 200 is worn on the user. For example, the first surface 210a may form at least a portion of the exterior of the first frame 211. The second surface 210b, which is opposite to the first surface 210a, may form at least a portion of the exterior of the second frame 212.

For example, the first frame 211 may be referred to as an 'inner wall' of the housing 210 in that the wearable device 200 is in contact with a part 20 of the user's body while worn on the user. The first surface 210a of the first frame 211 may be referred to as an 'inner surface' of the housing 210 in that the wearable device 200 surrounds at least partially the part 20 of the user's body on which the wearable device 200 is worn. For example, the second frame 212 may be referred to as an 'outer wall of the housing 210, in terms of being coupled with the first frame 211 to surround the first frame 21. The second surface 210b of the second frame 212 may be referred to as an 'outer surface' of the housing 210, in that it is a periphery that does not contact with the part 20 of the body on which the wearable device 200 is worn while the wearable device 200 is worn on the user. For example, referring to FIG. 2B together, the first frame 211 may provide a medium for a path of light emitted from a light emitter 251. The first frame 211 may include at least one of silicon, epoxy, and acryl, but is not limited thereto.

For example, the second frame 212 may surround the first frame 211. For example, the second frame 212 may support the first frame 211. For example, the second frame 212 may form the exterior of the housing 210 together with the first frame 211. For example, the second frame 212 may be a portion of the housing 210, which includes the second surface 210b opposite to the first surface 210a. The second frame 212 may include at least one of metal and titanium, but is not limited thereto. The housing 210 of the wearable device 200 may provide various user experience to the user, by including the first frame 211 and the second frame 212, which include different materials.

Referring to FIG. 2B, the wearable device 200 may include electronic components in the housing 210 to perform a function of the wearable device 200. For example, the wearable device 200 may include a processor 201 (or, one or more processors), a communication circuit 202, a memory 203, an antenna 204, and a power management circuit 205. According to an embodiment, the power management circuit 205 may be implemented as at least a portion of a power management integrated circuit (PMIC).

According to an embodiment, the wearable device 200 may include a battery 230 for charging the wearable device 200 and a printed circuit board (PCB) 240 in a housing 210 connected to the battery 230. For example, the processor 201, the communication circuit 202, the memory 203, and the power management circuit 205 may be mounted on the printed circuit board 240. The power management circuit 205 may be configured to manage power supplied to the wearable device 200. For example, the battery 230 may include a charging interface 235 connected to the printed circuit board 240 and configured to receive power from an external power source to charge the battery 230. The battery 230 may be charged through the power supplied through the charging interface 235. The battery 230 may supply power to at least a portion of electronic components on the printed circuit board 240, by being connected to the printed circuit board 240.

According to an embodiment, the printed circuit board 240 may include at least one of a flexible printed circuit board (FPCB) and a rigid flexible printed circuit board (RFPCB), according to material thereof, but is not limited thereto.

The processor 201 may be configured to control at least a portion of electronic components in the wearable device 200. The processor 201 may control the electronic components in the wearable device 200 through communication with an external electronic device (e.g., the electronic device 101 of FIG. 1) connected to the wearable device 200.

The communication circuit 202 may connect the external electronic device 101 and the wearable device 200. The processor 201 may control at least a portion of the electronic components in the wearable device 200 or cause an event for executing a function of the external electronic device 101, through the communication circuit 202, based on a user input inputted to the external electronic device 101. For example, the processor 201 of the wearable device 200 may be configured to execute an application of the external electronic device 101, through the communication circuit 202 and a processor (e.g., the processor 120 of FIG. 1) in the external electronic device 101. However, it is not limited thereto.

According to an embodiment, the communication circuit 202 may connect the wearable device 200 to the external electronic device 101 through near field communication. For example, the communication circuit 202 may connect the wearable device 200 and the external electronic device 101, based on the external electronic device 101 within a designated distance range from the wearable device 200. However, it is not limited thereto. The communication circuit 202 may establish a wireless communication network for communication with the external electronic device 101, through Wi-Fi, NFC, Zigbee, Bluetooth, Radio Frequency Identification (RFID), or any combination thereof. The communication circuit 202 may transmit a user input to the wearable device 200 to the external electronic device 101, or receive a user input to the external electronic device 101 from the external electronic device 101, through a short-range wireless communication network between the wearable device 200 and the external electronic device 101.

The electronic components included in the wearable device 200 are not limited to the above-described configurations. For example, the wearable device 200 may include various sensors including a temperature sensor, a proximity sensor, a motion sensor, and a pressure sensor.

According to an embodiment, the wearable device 200 may include a first sensor module 250 including a light emitter 251 facing the first surface 210a of the housing 210 and a light receiver 252 spaced apart from the light emitter 251, and configured to detect biometric information of the user.

According to an embodiment, the processor 201 may be configured to emit light using the light emitter 251 of the first sensor module 250. The processor 201 may be configured to obtain information related to an external environment through at least a portion of light received by the light receiver 252 after being emitted from the light emitter 251, by using the light receiver 252 of the first sensor module 250.

For example, the first sensor module 250 may be disposed in an inner space of the housing 210 between the first surface 210a and the second surface 210b. For example, the first sensor module 250 may be disposed on a component (e.g., the printed circuit board 240) of the wearable device 200 between the first surface 210a and the second surface 210b. The first sensor module 250 may be electrically connected to the component. For example, the first sensor module 250 may be configured to sense the user's state by using the part 20 of the user's body worn on the wearable device 200. The wearable device 200 may be configured to provide information related to the state to the user, through the sensed the user's state. For example, the first sensor module 250 may include at least one of an optical sensor or a heartrate measurement (HRM) sensor using photoplethysmography (PPG), but is not limited thereto. The light emitter 251 may be referred to as a light emitting diode (LED), and the light receiver 252 may be referred to as a photo diode, but is not limited thereto.

For example, the light emitter 251 may be configured to emit light in a plurality of directions. A portion of light emitted from the light emitter 251 in the plurality of directions may be reflected by the part 20 of the user's body worn on the electronic device 101. For example, the light emitter 251 may be configured to emit light toward the part 20 of the user's body on which the wearable device 200 is worn. The light emitted from the light emitter 251 toward the part 20 of the user's body may be reflected by the part 20 of the body.

For example, the light receiver 252 may be configured to receive a portion of the light emitted from the light emitter 251 in the plurality of directions. For example, the light emitter 251 may be configured to emit light toward the part 20 of the user's body on which the electronic device 101 is worn. The light receiver 252 may be configured to receive a portion of light reflected by the part 20 of the user's body. The light receiver 252 may be configured to receive the portion of the light through a space and/or medium between the first surface 210a and the second surface 210b of the housing 210.

For example, the first sensor module 250 may be configured to detect a state of the user, based on that the light emitted from the light receiver 252 and reflected by the part 20 of the user's body is received by the light receiver 252. The electronic device 101 may be configured to obtain information related to the user's state from the sensor module 250. For example, the light emitter 251 may emit light toward the first body part 21 of the user on which the wearable device 200 is worn. The light receiver 252 may receive at least a portion of light emitted from the light emitter 251 and reflected by the first body part 21. The first sensor module 250 may be configured to detect the user's state through at least a portion of the light reflected by the first body part 21.

According to an embodiment, the light emitter 251 may include a plurality of light emitters 251a, 251b, and 251c. The plurality of light emitters 251a, 251b, and 251c may face the first surface 210a of the housing 210, so as to emit light, respectively, toward the part 20 of the user's body in which the wearable device 200 is worn. According to an embodiment, the light receiver 252 may include a plurality of light receivers 252a, 252b, and 252c. Each of the plurality of light receivers 252a, 252b, and 252c may face the first surface 210a of the housing 210, in order to receive at least a portion of light emitted from the light emitter 251 and reflected by the part 20 of the user's body wearing the wearable device 200, respectively.

According to an embodiment, in order to provide various user experiences to the user, the wearable device 200 may be required to cause an event for executing a function of an external electronic device 101 connected to the wearable device 200 through a motion of the part 20 of user's body and/or the user's biometric information (e.g., fingerprint), based on the wearable device 200 being worn on the part 20 of the user's body. A structure of the wearable device 200 for executing the function of the external electronic device 101 connected to the wearable device 200 through the user's motion and/or the user's biometric information will be described later in FIG. 3A.

According to an embodiment described above, the wearable device 200 may be capable of being worn on the part 20 of the user's body to provide various user experiences to the user. The wearable device 200 may be configured to increase the user's wearability and provide information related to the user to the user, by including the housing 210 including the first surface 210a configured to face the part 20 of the user's body.

Figure 3A:
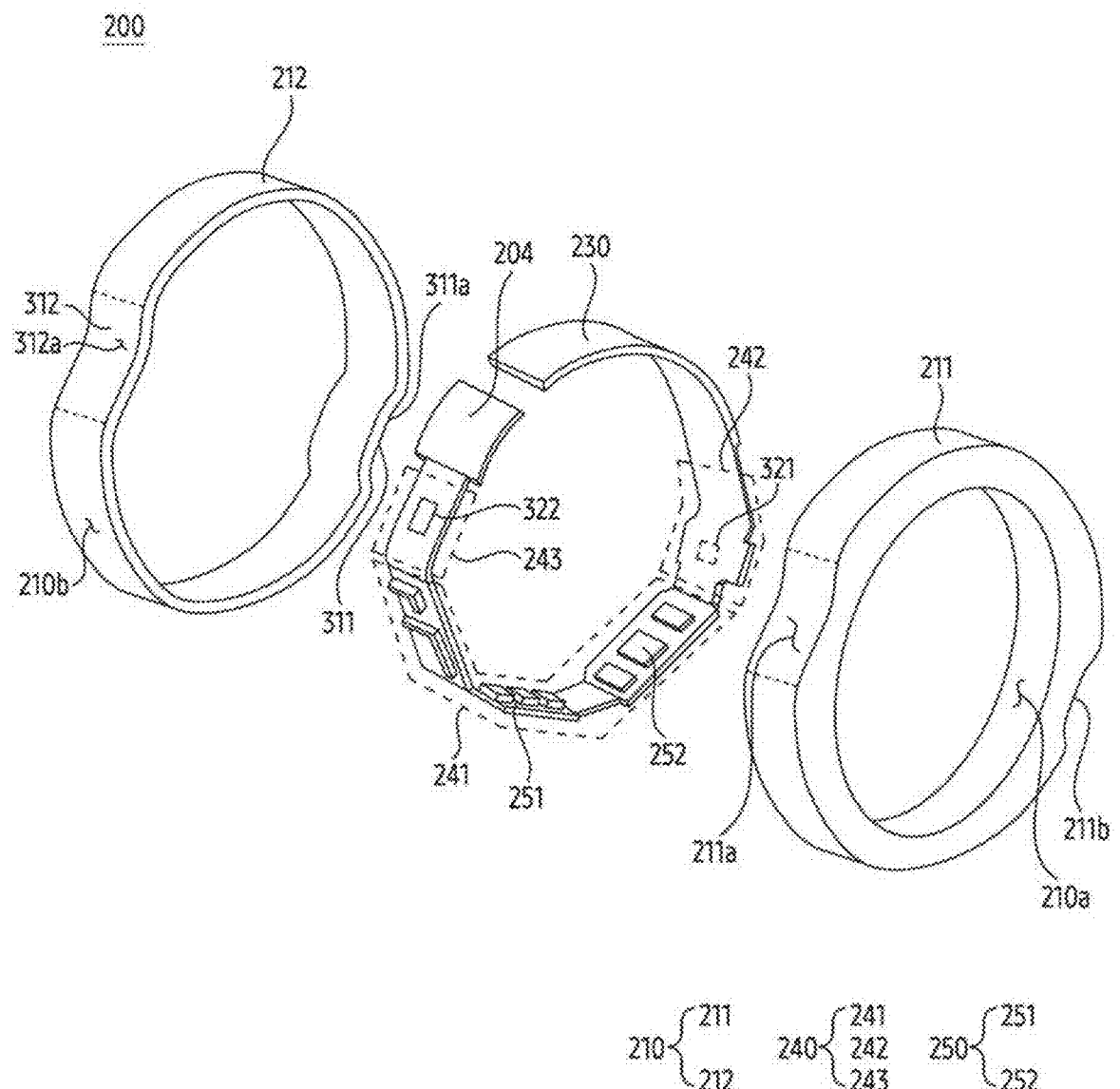
FIG. 3A is an exploded perspective view of an exemplary wearable device.
Figure 3B:
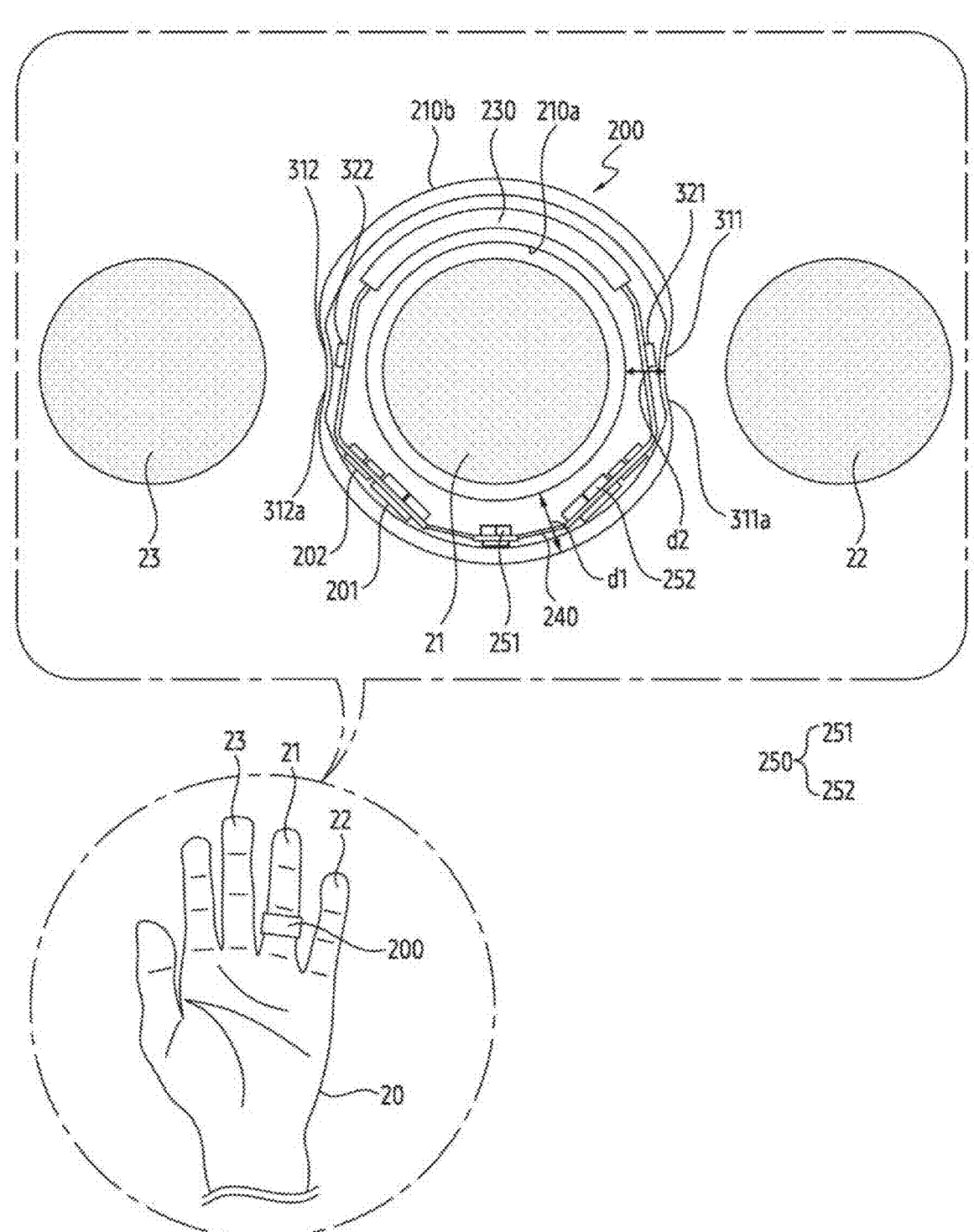
FIGS. 3B and 3C illustrate an exemplary wearable device worn on a user.
Figure 3C:
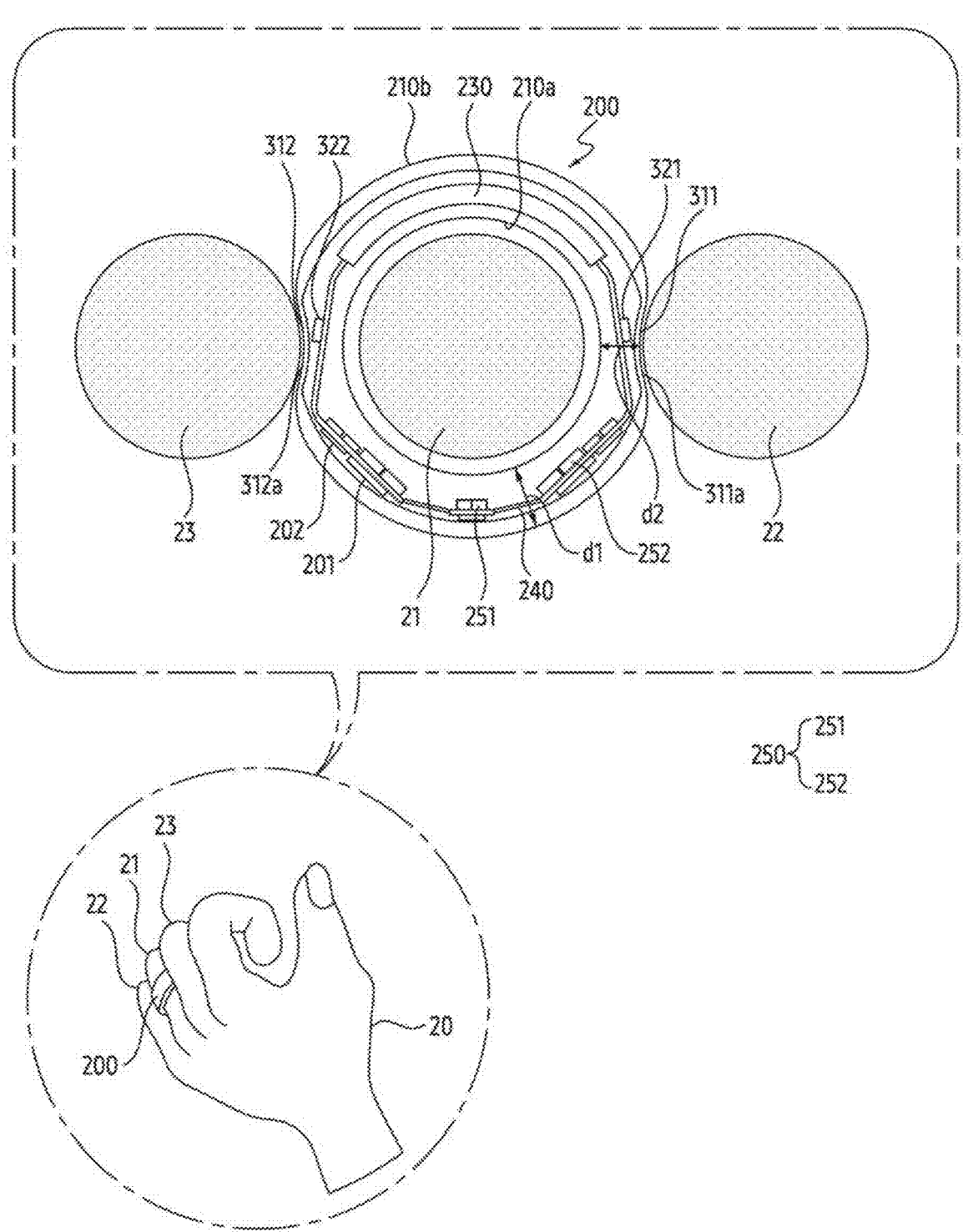
Figure 3D:
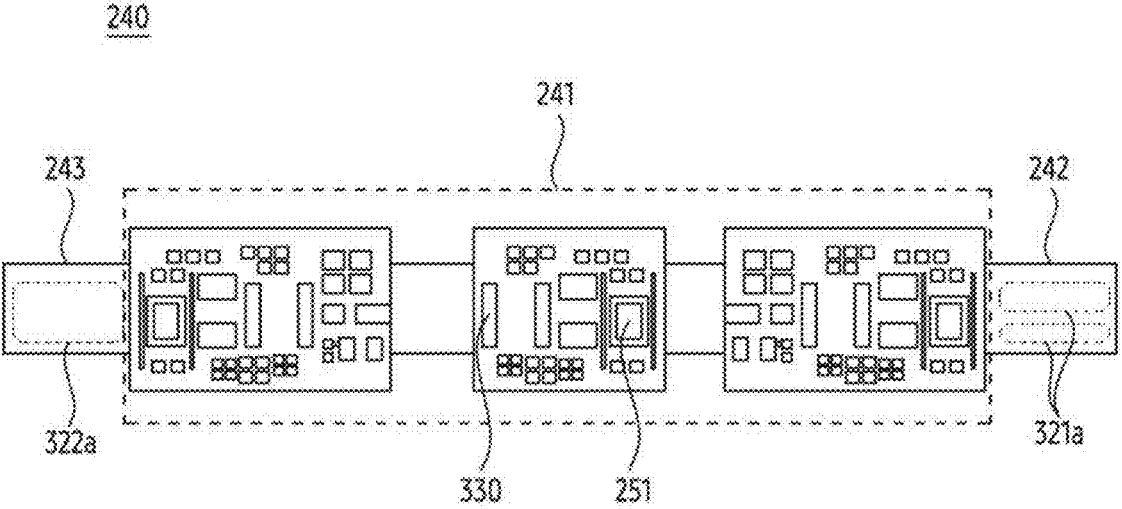
FIG. 3D is a top plan view of a printed circuit board of an exemplary wearable device.

FIG. 3A is an exploded perspective view of an exemplary wearable device. FIGS. 3B and 3C illustrate an exemplary wearable device worn on a user. FIG. 3D is a top plan view of a printed circuit board of an exemplary wearable device.

Referring to FIGS. 3A, 3B, 3C, and 3D, while a wearable device 200 is worn on a first body part 21 of a user, the wearable device 200 may include a housing 210 including a first surface 210a facing the first body part 21 and a second surface 210b opposite to the first surface 210a. According to an embodiment, the wearable device 200 may include a battery 230 in the housing 210 and a printed circuit board 240 connected to the battery 230. According to an embodiment, the housing 210 may include a first frame 211 defining the first surface 210a, and a second frame 212 defining the second surface 210b and coupled to the first frame 211.

According to an embodiment, the housing 210 may include a groove 311 formed from the second surface 210b toward the first surface 210a. For example, the groove 311 may be formed in the second frame 212 defining the second surface 210b from among the first frame 211 and the second frame 212 of the housing 210. For example, groove 311 may provide a space for accommodating the user's another body part (e.g., a second body part 22) distinct from the first body part 21 in which the wearable device 200 is worn. For example, the groove 311 may be located on at least a portion of the printed circuit board 240. For example, the groove 311 may be formed on the second surface 210b.

According to an embodiment, the wearable device 200 may include a first sensor 321 in the housing 210 facing the groove 311 of the housing 210. The first sensor 321 may be configured to detect the user's second body part 22 distinct from the user's first body part 21 on which the wearable device 200 is worn, and positioned in the groove 311. For example, the first sensor 321 may be disposed between the first surface 210a of the housing 210 and the groove 311. For example, the first sensor 321 may be mounted on the printed circuit board 240. The first sensor 321 may be disposed on a portion of the printed circuit board 240 facing the groove 311. For example, the first sensor 321 may include a first electrode (321a of FIG. 3C). The first sensor 321 may be configured to detect the user's second body part 22 positioned in the groove 311 through the first electrode 321a. For example, the first sensor 321 may be configured to detect the second body part 22 positioned in the groove 311, by being disposed adjacent to the user's second body part 22 positioned in the groove 311 through the groove 311. For example, the first sensor 321 may include at least one of a touch sensor and a distance sensor, but is not limited thereto.

According to an embodiment, the first sensor 321 may be disposed in the first frame 211 of the housing 210. For example, the first frame 211 may include a curved surface 211b for accommodating the groove 311 of the second frame 212. The first sensor 321 may be disposed between the first surface 210a of the first frame 211 and the curved surface 211b. For example, the first sensor 321 may be disposed in the housing 210 to face the curved surface 211b of the first frame 211 to be coupled to the groove 311.

According to an embodiment, the groove 311 may include a curved surface 311a having a curvature in order to accommodate at least a portion of the user's second body part 22 by being bent at least partially. For example, the curved surface 311a may be formed in the second frame 212. The curved surface 311a may correspond to the curved surface 211b in the first frame 211 for accommodating the groove 311. By including the curved surface 311a, the groove 311 may improve the wearability of the wearable device 200 for the user while the user's second body part 22 is positioned in the groove 311.

For example, the groove 311 of the wearable device 200 may be referred to as a recess for accommodating another body part (e.g., the second body part 22) distinct from the first body part 21 of the user, or for fingerprint authentication through the other body part, while the wearable device 200 is worn on the user's first body part 21. The groove 311 may form a cavity for accommodating the other body part, by including the curved surface 311a.

According to an embodiment, a distance d1 between the first surface 210a and the second surface 210b may be greater than a distance d2 between the first surface 210a and the groove 311. As the distance d1 is greater than the distance d2, the groove 311 may provide a space for accommodating the user's second body part 22 to the user. According to an embodiment, the distance d1 between the first surface 210a and the second surface 210b may be located within a range of approximately 2 mm or more and approximately 3 mm or less, and a depth of the groove 311 may be located within a range of approximately 0.2 mm or more and approximately 1.5 mm or less.

According to an embodiment, the printed circuit board 240 may include a first region 241 including at least one electronic component, and a second region 242 between the first surface 210a connecting the first region 241 and the battery 230 and the groove 311. The first sensor 321 may be fastened to the second region 242. For example, the processor 201 and the communication circuit 202 may be mounted in the first region 241. For example, the first region 241 may be a region of the printed circuit board 240 facing the battery 230 and spaced apart from the battery 230. For example, a first sensor module 250 including a light emitter 251 and a light receiver 252 spaced apart from the light emitter 251 may be disposed on the first region 241. For example, the second region 242 may be connected from the first region 241 to the battery 230. The thickness of the second region 242 may be smaller than the average thickness of the first region 241. For example, the second region 242 may face the groove 311. The second region 242 may be disposed under the groove 311. For example, the second region 242 may have flexibility, but is not limited thereto. For example, the first sensor 321 may be disposed on a surface of the second region 242 facing the groove 311 of the housing 210 among the second region 242 of the printed circuit board 240. The first sensor 321 may be disposed to face the groove 311 and be adjacent to the groove 311, by being disposed on the second region 242.

According to an embodiment, the housing 210 may face the groove 311 and may include another groove 312 formed from the second surface 210b toward the first surface 210a and spaced apart from the groove 311. The wearable device 200 may further include a second sensor 322 in the housing 210 facing the other groove 312. The second sensor 322 may be configured to detect the user's third body part 23 positioned in the other groove 312 and distinguished from the first body part 21 on which the wearable device 200 is worn and the second body part 22 positioned in the groove 311.

For example, the other groove 312 may be configured to be substantially the same as or similar to the groove 311. For example, the other groove 312 may be space apart from the groove 311 while facing. For example, the other groove 312 may overlap the groove 311 when the groove 311 is viewed from above. For example, the other groove 312 may include a curved surface 312a bent by having a curvature. The other groove 312 may be configured to accommodate the third body part 23 distinct from the user's first body part 21 and the second body part 22, through the curved surface 312a. For example, the other groove 312 may be formed in the second frame 212 of the housing 210. The first frame 211 coupled to the second frame 212 may include the curved surface 211a to be coupled to the other groove 312, in order to correspond to the curved surface 312a of the other groove 312. The curved surface 211a may face the curved surface 211b facing the groove 311.

For example, the second sensor 322 may face the other groove 312. For example, the second sensor 322 may be configured to be substantially the same as or similar to the first sensor 321. For example, the printed circuit board 240 may include a third region 243 connecting the antenna 204 and the first region 241. The third region 243 may be disposed between the first surface 210a and the other groove 312. The second sensor 322 may be disposed on a surface of the third region 243 facing the other groove 312. For example, the average thickness of the third region 243 on which the second sensor 322 is disposed may be smaller than the average thickness of the first region 241. For example, the second sensor 322 may include a second electrode (322a of FIG. 3C). Through the second electrode 322a, the second sensor 322 may be configured to detect the user's third body part 23 positioned in the other groove 312.

According to an embodiment, the first sensor 321 and the second sensor 322 of the wearable device 200 may be referred to as a touch sensor, respectively. For example, in order to detect contact with at least a portion of the user's body parts 21, 22, and 23, the first sensor 321 and/or the second sensor 322 may include a resistive touch screen sensor, a capacitive touch sensor, a surface acoustic wave touch screen sensor, an infrared touch screen sensor, or a combination thereof, but is not limited thereto. For example, the first sensor 321 and/or the second sensor 322 may be configured to detect that at least a portion of the user's body parts 21, 22, and 23 of are in contact with the groove 311 and/or the other groove 312, by detecting changes in capacitance and/or resistance through the first electrode 321a and the second electrode 322a, respectively.

According to an embodiment, the wearable device 200 may include the first sensor module 250 configured to detect biometric information of the user and including the light emitter 251 facing the first surface 210a and the light receiver 252 spaced apart from the light emitter 251, and the processor 201. The processor 201 may be configured to emit light using the light emitter 251 of the first sensor module 250. The processor 201 may be configured to obtain information related to an external environment through at least a portion of the light received by the light receiver 252 after being emitted from the light emitter 251, by using the light receiver 252 of the first sensor circuit 250. The processor 120 may be configured to identify whether the wearable device 200 is worn on the user's first body part 21 through at least a portion of the light received by the light receiver 252. The processor 201 may be configured to operate the first sensor 321, based on identifying the wearable device 200 worn on the first body part 21. For example, the light receiver 252 may be configured to receive at least a portion of light emitted from the light emitter 251 and reflected by the first body part 21 on which the wearable device 200 is worn. The processor 201 may be configured to identify that the wearable device 200 is worn on the first body part 21, based on at least a portion of the light detected through the light receiver 252 and reflected by the first body part 21. The processor 201 may be configured to operate the first sensor 321 and/or the second sensor 322, based on identifying that the wearable device 200 is worn on the first body part 21. For example, the processor 201 may be configured to supply power to the first sensor 321 and/or the second sensor 322 through the battery 230 and/or a power management circuit (e.g., the power management circuit 205 of FIG. 2B), based on identifying that the wearable device 200 is worn on the first body part 21. The wearable device 200 may detect a touch of a part of the user's body (e.g., the second body part 22 and/or the third body part 23 of FIG. 3B) to the groove 311 and/or another groove 312 of the wearable device 200, through the first sensor 321 and/or the second sensor 322.

According to an embodiment, the wearable device 200 may include the communication circuit 202 for communication with an external electronic device (e.g., the electronic device 101 of FIG. 1) and a third sensor (330 of FIG. 3C) configured to detect the user's motion through the user's first body part 21 wearing the wearable device 200. For example, the third sensor 330 may be disposed in the first region 241 of the printed circuit board 240. For example, the third sensor 330 may include at least one of a gyro sensor and an acceleration sensor, but is not limited thereto. The wearable device 200 may provide various user experiences to a user of the wearable device 200 by including the third sensor 330. The wearable device 200 providing various user experiences through the third sensor 330 will be described later with reference to FIG. 6A.

According to an embodiment, the third sensor 330 may be referred to as an accelerometer and/or a gyro sensor for detecting a motion of a user wearing the wearable device 200. For example, the third sensor 330 may detect the user's motion, based on moving of the user's first body part 21 and/or inclination of the wearable device 200 according to the moving of the first body part 21. For example, the third sensor 330 may detect the user's motion, based on rotation of the first body part 21 and/or a moving speed of the first body part 21 of the user wearing the wearable device 200. However, it is not limited thereto.

According to an embodiment, in a state in which the wearable device 200 is worn on the first body part 21, the second body part 22 may be in contact with the groove 311 or the third body part 23 may be in contact with another groove 312, contrary to the user's intention. The wearable device 200 may include a component for reducing the sensing of the first sensor 321 and/or the sensing of the second sensor 322 that is not intended by the user, or may perform an operation to reduce malfunctions of the first sensor 321 and the second sensor 322.

According to an embodiment, each of the first sensor 321 and/or the second sensor 322 may be a force sensor. Through the first sensor 321, the processor 201 of the wearable device 200 may be configured to detect the second body part 22 positioned in the groove 311, based on that a force pressurizing the groove 311 is greater than or equal to a designated value. Through the second sensor 322, the processor 201 of the electronic device 200 may be configured to detect the third body part 23 positioned in the other groove 312, Based on that the force pressurizing the other groove 312 is greater than or equal to the designated value. For example, the first sensor 321 and/or the second sensor 322 may be a touch sensor. The third sensor 330 may be a gyro sensor or an acceleration sensor for detecting the user's moving. The first sensor 321 and the second sensor 322 for sensing a touch may be configured to detect the second body part 22 positioned in the groove 311 and/or the third body part 23 positioned in the other groove 312, based on detecting a motion corresponding to a preset gesture, by being linked with the third sensor 330 for detecting the user's motion. However, it is not limited thereto.

According to the above-described embodiment, the wearable device 200 may increase the user's wearability of the wearable device 200 by including the groove 311. The wearable device 200 may be configured so that the processor 201 of the wearable device 200 identifies whether the wearable device 200 is worn on the user, by including the first sensor module 250. The wearable device 200 may provide various user experiences to the user, by including the first sensor 321 in the housing 210 facing the groove 311.

Figure 4:
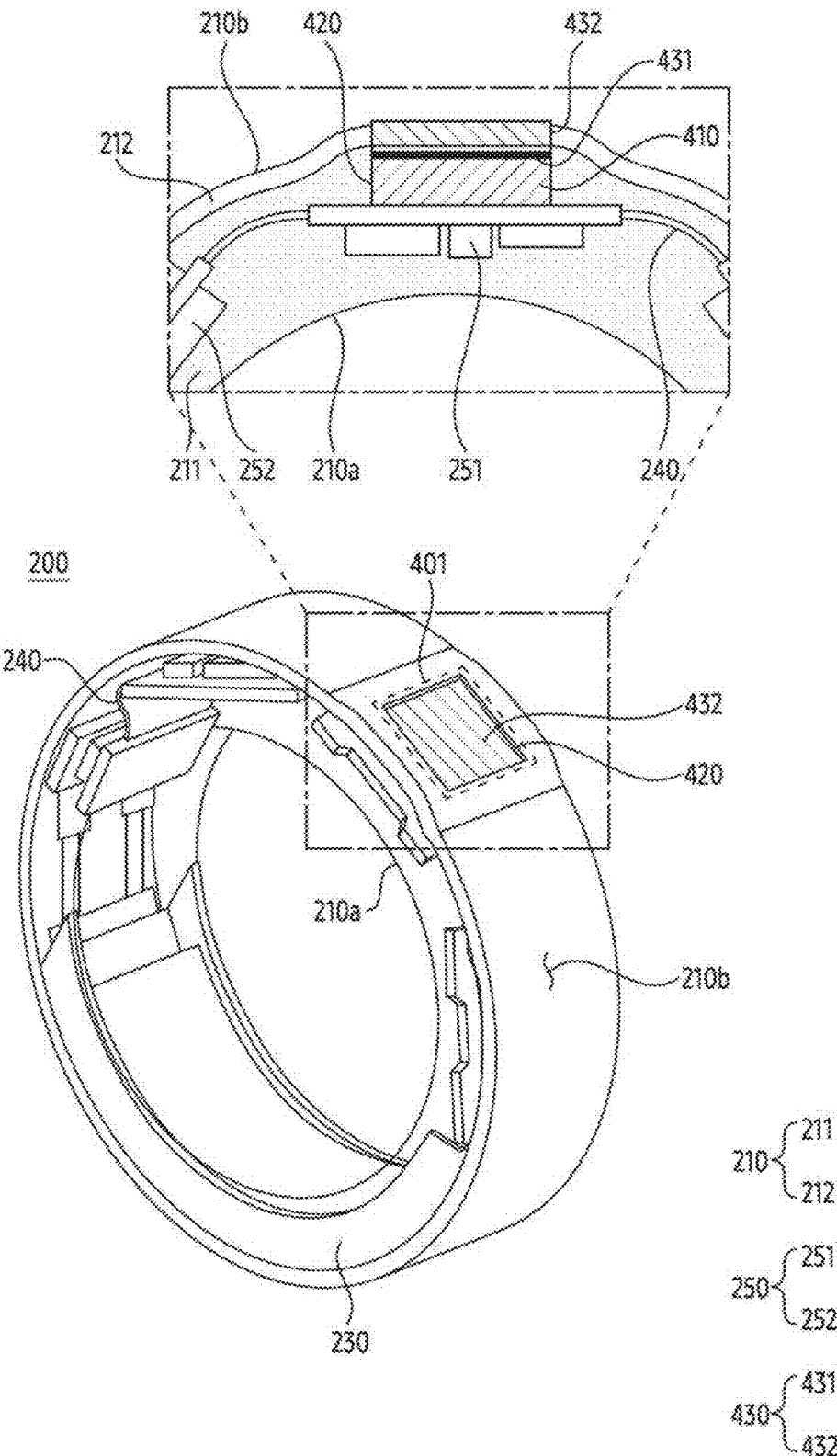
FIG. 4 illustrates an exemplary wearable device.

FIG. 4 illustrates an exemplary wearable device.

Referring to FIG. 4, while a wearable device 200 is worn on a user's first body part (e.g., the first body part 21 of FIG. 2A), the wearable device 200 may include a housing 210 including a first surface 210a facing the first body part 21 and a second surface 210b opposite to the first surface 210a. The wearable device 200 may include a first sensor circuit 250 including a light emitter 251 facing the first surface 210a and a light receiver 252 spaced apart from the light emitter 251, and configured to detect biometric information of the user, and a processor (e.g., the processor 201 of FIG. 2A). The processor 201 may be configured to emit light using the light emitter 251 of the first sensor module 250. The processor 201 may be configured to obtain information related to an external environment through at least a portion of the light received by the light receiver 252 after being emitted from the light emitter 251, by using the light receiver 252 of the first sensor module 250. According to an embodiment, the wearable device 200 may include a battery 230 in the housing 210 and a printed circuit board 240 connected to the battery 230. According to an embodiment, the housing 210 may include a first frame 211 defining the first surface 210a and a second frame 212 defining the second surface 210b and coupled to the first frame 211.

According to an embodiment, the wearable device 200 may include a second sensor module 410 in the housing 210 configured to detect a user's fingerprint and facing the second surface 210b. The second sensor module 410, similarly with the first sensor module, may include at least one light emitter and at least one light receiver configured to receive at least a portion of the light emitted from the at least one light emitter of the second sensor module 410. For example, the second sensor module 410 may be disposed in the first frame 211 of the housing 210. For example, the second sensor module 410 may be disposed on the printed circuit board 240. The second sensor module 410 may be disposed between the printed circuit board 240 and the second surface 210b of the housing 210. For example, the second sensor module 410 may be disposed on a surface of the printed circuit board 240 facing the second frame 212.

According to an embodiment, the wearable device 200 may include a plurality of optical sensors. For example, the wearable device 200 may include the first sensor module 250 of FIG. 2B and/or the second sensor module 410 of FIG. 4. Each of the sensor modules 250 and 410 may include a light emitter (e.g., the light emitter 251 of FIG. 2B) for emitting light and a light receiver (e.g., the light receiver 252 of FIG. 2B). The light emitter may be referred to as a Light Emitting Diode (LED), and the light receiver may be referred to as a photo diode (PD), but is not limited thereto. The sensor modules 250 and 410 may include at least one of an optical sensor or a heartrate measurement (HRM) sensor using photoplethysmography (PPG), but is not limited thereto. For example, the first sensor module 250 may obtain the user's biometric information (e.g., blood flow speed), based on emitting light toward a finger (e.g., the first body part 21 of FIG. 2A) of the user on which the wearable device 200 is worn and receiving at least a portion of the light reflected from the user's finger. The first sensor module 250 may identify whether the wearable device 200 is worn on the user based on the measured biometric information. For example, the second sensor module 410 may obtain the user's biometric information (e.g., fingerprint), based on emitting light toward the user's finger (e.g., the fourth body part 71 of FIG. 7B) located on a fingerprint authentication region 401 provided by a second cover member 432, and receiving at least a portion of the light reflected from the user's finger. The processor 201 may be configured to perform an event for fingerprint authentication based on the biometric information obtained through the second sensor module 410. However, it is not limited thereto, and the wearable device 200 may include a plurality of optical sensors for obtaining the user's biometric information according to a function thereof.

For example, the second sensor module 410 may include a light emitter configured to emit light and a light receiver configured to receive at least a portion of the light emitted from the light emitter. The light emitter of the second sensor module 410 may emit light toward a part (e.g., a fourth body part 71 of FIG. 7B) of the user's body located on the second sensor module 410. The light receiving unit of the second sensor module 410 may be configured to detect a fingerprint included in the part of the user's body by receiving at least a portion of the light reflected by the part of the user's body. However, it is not limited thereto.

According to an embodiment, the wearable device 200 may include a hole 420 connected to the second sensor module 410 by extending from the second surface 210b to inside of the housing 210, and at least one cover member 430 disposed on the second sensor module 410 and covering the hole 420.

For example, the hole 420 may penetrate the second frame 212. The hole 420 may penetrate a portion of the first frame 211 coupled to the second frame 212. For example, the hole 420 may overlap the second sensor module 410 when the hole 420 is viewed from above. For example, the hole 420 may extend from the second surface 210b of the housing 210 to a surface of the printed circuit board 240 on which the second sensor module 410 is mounted. For example, an inner surface of the hole 420 may be in contact with the second sensor module 410. The inner surface of the hole 420 may surround at least a portion of the second sensor module 410. For example, the hole 420 may provide a seating space for the second sensor module 410. For example, the hole 420 may provide a passage for light emitted from the second sensor module 410.

For example, the at least one cover member 430 may cover the second sensor module 410. For example, the at least one cover member 430 may shield the second sensor module 410 by covering the hole 420. For example, the at least one cover member 430 may include a first cover member 431 in contact with the second sensor module 410 and a second cover member 432 facing the first cover member 431 and exposed to the outside. The first cover member 431 may be attached to a surface of the second sensor module 410 facing the outside. The second cover member 432 may cover the hole 420 by being disposed on the first cover member 431. The second cover member 432 may be configured to provide a fingerprint authentication region 401 for the user's fingerprint authentication by being exposed to the outside. Since the second cover member 432 overlaps the second sensor module 410, when the user's fingerprint is located on the fingerprint authentication region 401 provided by the second cover member 432, the second sensor module 410 may detect the user's fingerprint.

According to the above-described embodiment, the wearable device 200 may provide various experiences to the user by including the second sensor module 410. The wearable device may provide a space in the wearable device 200 for the second sensor module 410 and provide a path for light emitted from the second sensor module 410, by including the hole 420 for the second sensor module 410. The wearable device 200 may cover the hole 420 by including the at least one cover member 430, and guide the user to a location of the second sensor module 410 for fingerprint authentication through the fingerprint authentication region 401.

Figure 5:
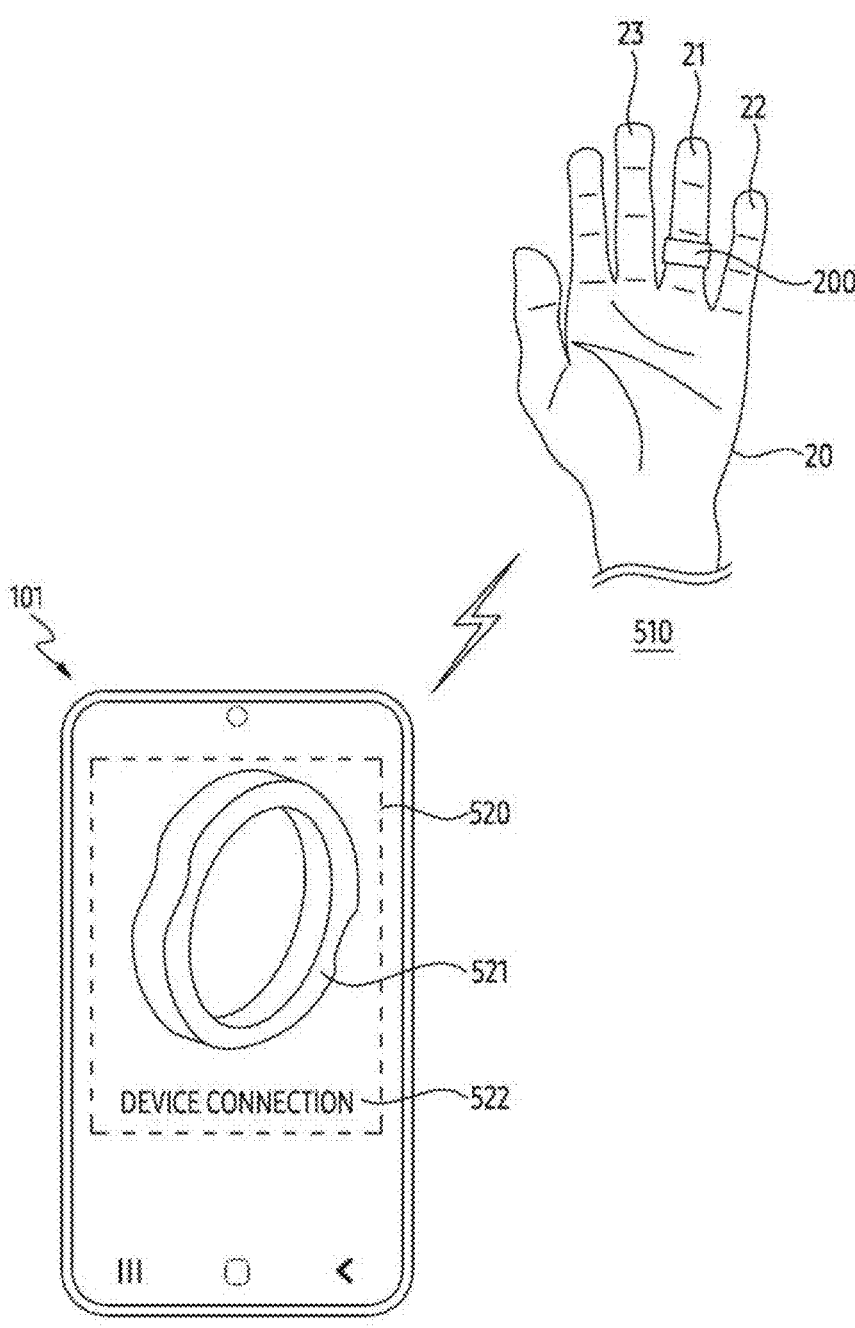
FIG. 5 illustrates an exemplary wearable device connected to an external electronic device.

FIG. 5 illustrates an exemplary wearable device connected to an external electronic device.

Referring to FIG. 5, a wearable device 200 may be worn on a first body part 21 among a part 20 of a body of a user. A housing (e.g., the housing 210 of FIG. 2A) of the wearable device 200 may include a first surface (e.g., the first surface 210a of FIG. 2a) facing the first body part 21 while the wearable device 200 is worn on the first body part 21, a second surface (e.g., the second surface 210b of FIG. 2A) opposite to the first surface 210a, and a groove (e.g., the groove 311 of FIG. 3A) formed from the second surface 210b toward the first surface 210a. According to an embodiment, the wearable device 200 may include a first sensor module (e.g., the first sensor module 250 of FIG. 2B) configured to detect biometric information of the user and including a light emitter facing the first surface 210a (e.g., light emitter 251 of FIG. 2B) and a light receiver (e.g., light receiver 252 of FIG. 2B) spaced apart from the light emitter 251. According to an embodiment, the housing 210 may include another groove (e.g., the other groove 312 of FIG. 3A) facing the groove 311. The wearable device 200 may include a first sensor (e.g., the first sensor 321 of FIG. 3A) configured to detect a user's second body part 22 distinct from the first body part 21 and positioned in the groove 311. The wearable device 200 may include a second sensor 322 configured to detect a user's third body part 23 distinct from the first body part 21 and the second body part 22 and positioned in the other groove 312. According to an embodiment, the wearable device 200 may include a processor (e.g., the processor 201 of FIG. 2B) and a communication circuit (e.g., the communication circuit 202 of FIG. 2B) for communication with an external electronic device 101.

Hereinafter, redundant descriptions of the configurations described in FIGS. 3A to 3C will be omitted.

In a state 510, the wearable device 200 may be worn on the user's first body part 21. The second body part 22 and the third body part 23 may be spaced apart from the wearable device 200. For example, the first body part 21 may be in contact with the wearable device 200. The second body part 22 and the third body part 23 distinct from the first body part 21 may not contact the wearable device 200.

According to an embodiment, in the state 510, the processor 201 of the wearable device 200 may identify the wearable device 200 worn on the user's first body part 21, through the first sensor module 250. For example, the processor 201 of the wearable device 200 may emit light by using the light emitter 251 of the first sensor module 250. At least a portion of light emitted from the light emitter 251 may be received to the light receiver 252 by being reflected by the first body part 21 of the user on which the wearable device 200 is worn. The processor 201 may identify the wearable device 200 worn on the user, through at least a portion of the light emitted from the light emitter 251 and reflected by the first body part 21. For example, the processor 201 may receive a signal related to an external environment of the wearable device 200 through the light received by the light receiver 252 of the first sensor module 250. As the wearable device 200 is worn on the user's first body part 21, the signal received by the light receiver 252 may be changed. The processor 201 may identify whether the wearable device 200 is worn on the user, through a change in the signal. For example, the processor 201 may identify the wearable device 200 worn on the user, based on identifying that intensity of the signal received by the light receiver 252 is the intensity greater than or equal to a threshold value.

According to an embodiment, the wearable device 200 may be connected to the external electronic device 101 through the communication circuit 202. In the state 510, the processor 201 may identify the wearable device 200 worn on the first body part 21 through the first sensor module 250. The processor 201 may be connected to the external electronic device 101 through the communication circuit 202, based on identifying the wearable device 200 worn on the first body part 21.

According to an embodiment, the processor 201 of the wearable device 200 may provide information indicating that the wearable device 200 is connected to the external electronic device 101, through the external electronic device 101 connected to the wearable device 200. For example, based on identifying that the wearable device 200 is worn on the first body part 21, the processor 201 may be configured to display a screen 520 of the external electronic device 101 through the communication circuit 202 and a processor (e.g., the processor 120 of FIG. 1) of the external electronic device 101. The screen 520 may include an image 521 and/or text

522 indicating that the wearable device 200 is connected to the external electronic device 101.

According to an embodiment, the processor 201 of the wearable device 200 may drive the first sensor 321 and/or the second sensor 322, based on identifying the wearable device 200 worn on the user's first body part 21. The processor 201 performing an event for executing a function of the external electronic device 101 through the first sensor 321 and the second sensor 322 will be described later with reference to FIG. 6A.

According to the above-described embodiment, the processor 201 of the wearable device 200 may be configured to identify whether the wearable device 200 is worn on the user through the first sensor module 250. The wearable device 200 may provide a user with various user experiences, by providing information indicating whether the wearable device 200 is worn on the user and/or whether the wearable device 200 is connected to the external electronic device 101, through the external electronic device 101 connected to the wearable device 200.

Figure 6A:
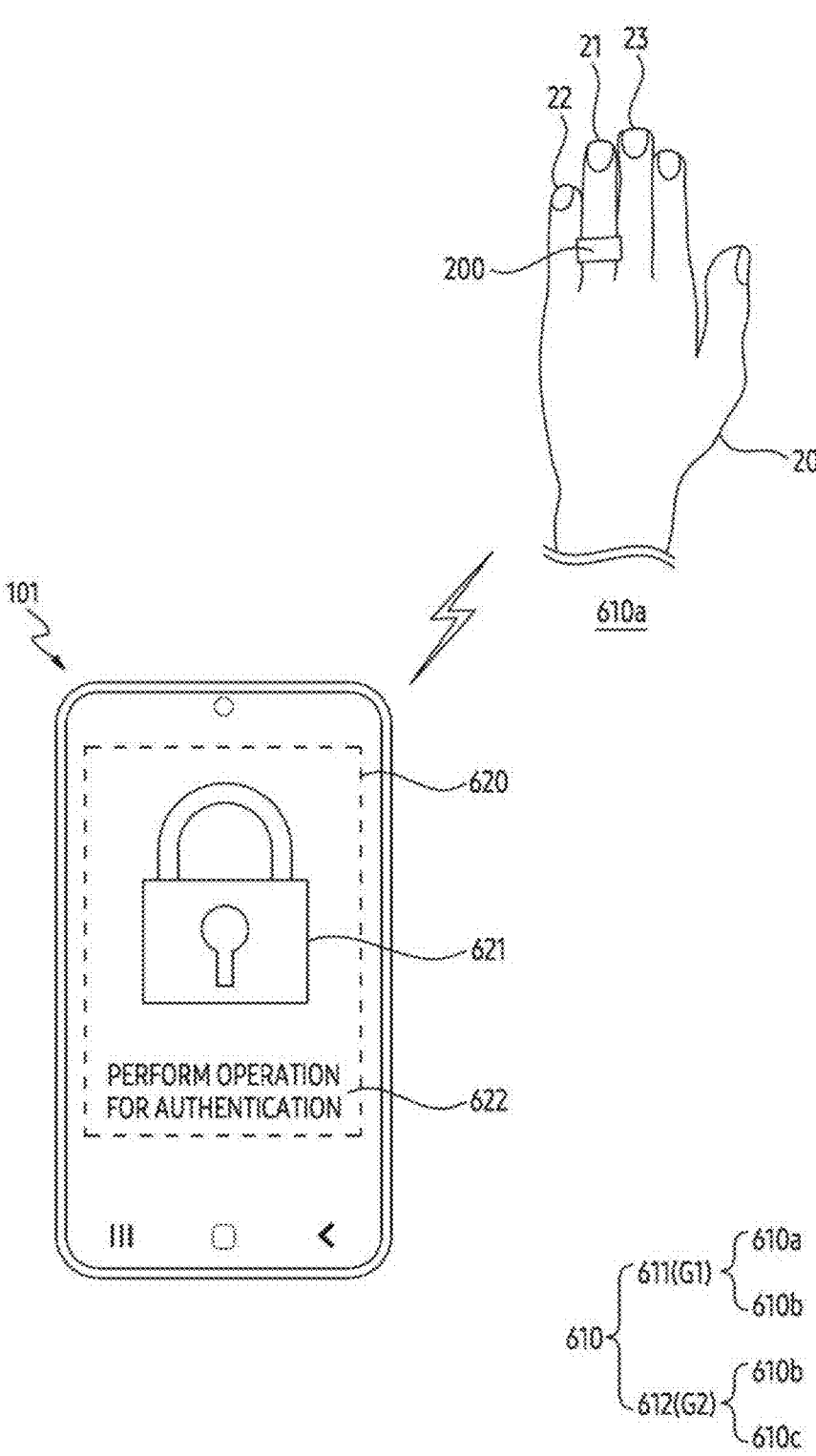
FIGS. 6A, 6B, and 6C illustrate an exemplary wearable device connected to an external electronic device.
Figure 6B:
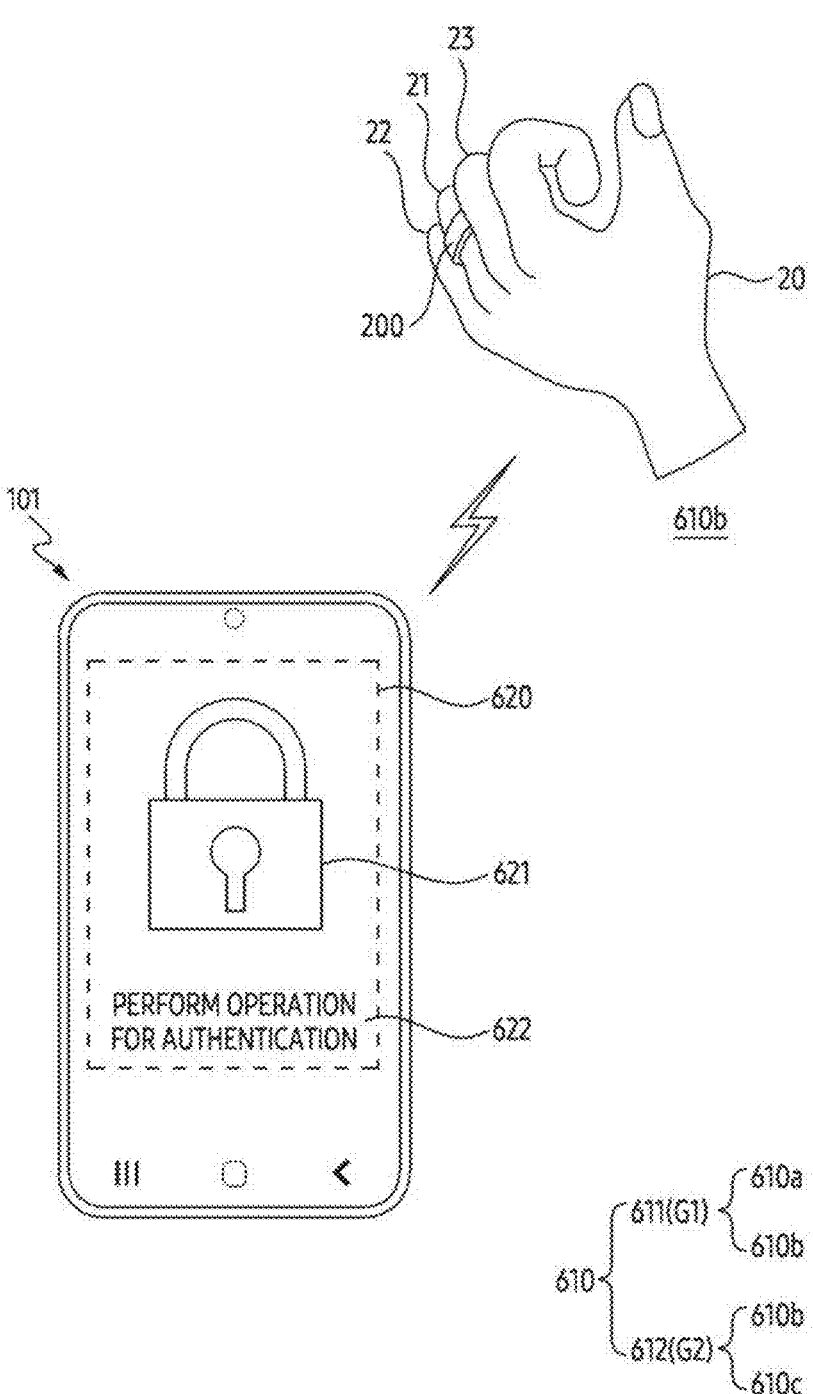
Figure 6C:
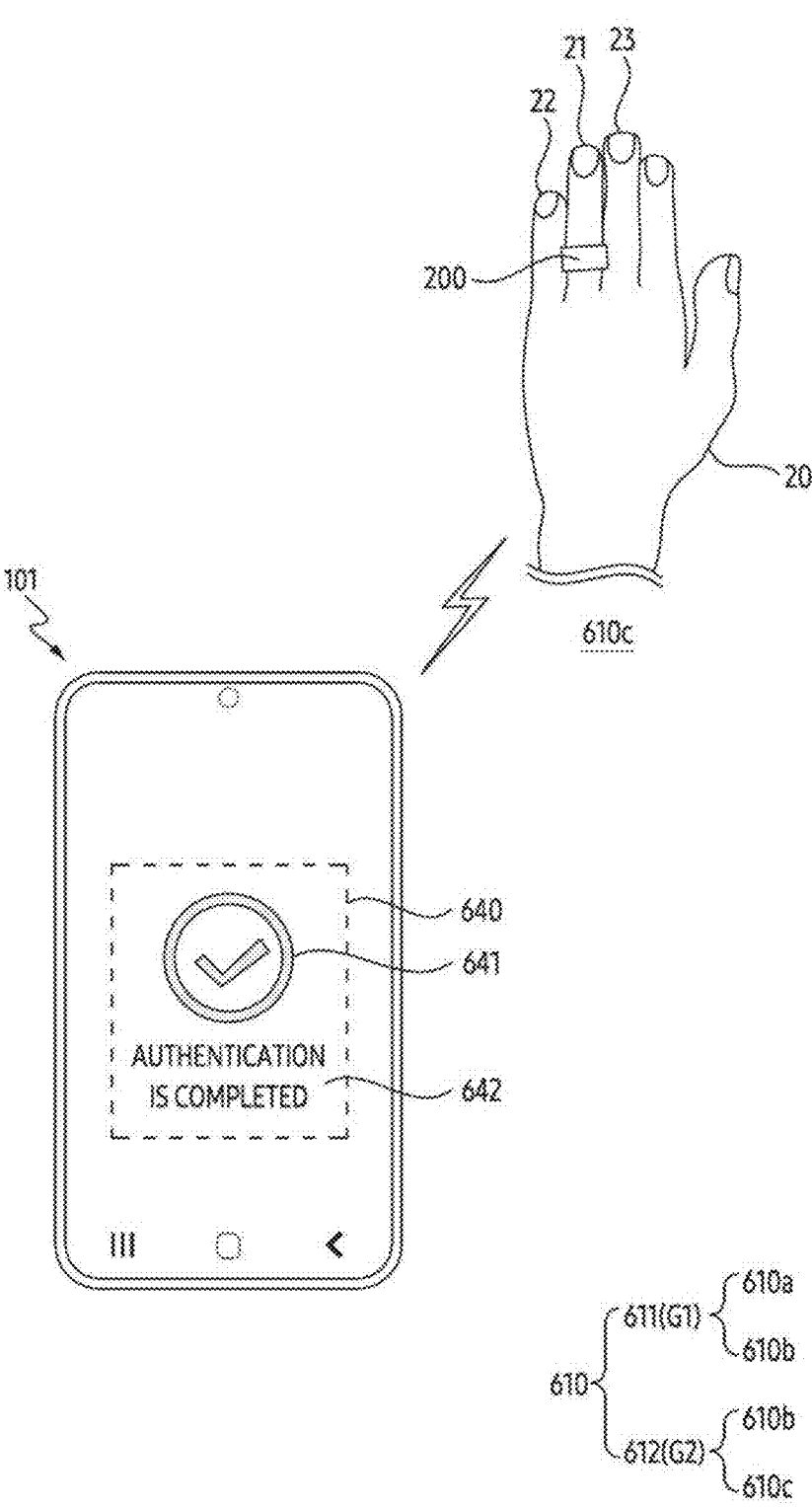

FIGS. 6A, 6B, and 6C illustrate an exemplary wearable device connected to an external electronic device.

Referring to FIGS. 6A, 6B, and 6C, a wearable device 200 may be worn on a first body part 21 of a part 20 of a user's body. A housing (e.g., the housing 210 of FIG. 2A) of the wearable device 200 may include a first surface (e.g., the first surface 210a of FIG. 2A) facing the first body part 21 while the wearable device 200 is worn on the first body part 21, a second surface (e.g., the second surface 210b of FIG. 2A) opposite to the first surface 210a, and a groove (e.g., the groove 311 of FIG. 3A) formed from the second surface 210b toward the first surface 210a. According to an embodiment, the wearable device 200 may include a first sensor module (e.g., the first sensor module 250 of FIG. 2B) configured to detect biometric information of the user, and including a light emitter (e.g., the light emitter 251 of FIG. 2B) facing the first surface 210a and a light receiver (e.g., the light receiver 252 of FIG. 2B) spaced apart from the light emitter 251. According to an embodiment, the housing 210 may include another groove (e.g., the other groove 312 of FIG. 3A) facing the groove 311. The wearable device 200 may include a first sensor (e.g., the first sensor 321 of FIG. 3A) configured to sense a user's second body part 22 distinct from the first body part 21 and positioned in the groove 311. The wearable device 200 may include a second sensor 322 configured to detect a user's third body part 23 distinct from the first body part 21 and the second body part 22 and positioned in the other groove 312. According to an embodiment, the wearable device 200 may include a processor (e.g., the processor 201 of FIG. 2B) and a communication circuit (e.g., the communication circuit 202 of FIG. 2B) for communication with the external electronic device 101.

According to an embodiment, the processor 201 of the wearable device 200 may identify the wearable device 200 worn on the first body part 21 through the first sensor module 250. Based on identifying the wearable device 200 worn on the first body part 21, the processor 201 may drive the first sensor 321 facing the groove 311 and the second sensor 322 facing the other groove 312.

According to an embodiment, the processor 201 of the wearable device 200 may identify the second body part 22 positioned in the groove 311 through the first sensor 321. The processor 201 may identify the third body part 23 positioned in the other groove 312 through the second sensor 322. The processor 201 may detect a touch of the second body part 22 to the groove 311 through the first sensor 321. The processor 201 may detect a touch of the third body part

23 to the other groove 312 through the second sensor 322. The processor 201 may be configured to perform an event for executing a function of the external electronic device 101 connected to the wearable device 200 through the communication circuit 202, based on identifying the second body part 22 positioned in the groove 311 and the third body part 23 positioned in the other groove 312. For example, the event may be an event for unlocking the external electronic device 101. However, it is not limited thereto.

According to an embodiment, the wearable device 200 may include a third sensor (e.g., the third sensor 330 of FIG. 3C) configured to detect a user's motion 610. The processor 201 of the wearable device 200 may identify the user's motion 610 through the third sensor, based on identifying the second body part 22 positioned in the groove 311 and/or the third body part 23 positioned in the other groove 312. The processor 201 may be configured to perform an event for executing a function of the external electronic device 101 corresponding to the user's motion 610, through the communication circuit 202, based on the user's motion 610.

For example, referring to FIGS. 6A and 6B, a first motion 611 may include moving of the part 20 of the user's body during a change from a state 610a to a state 610b. For example, in a state where a finger (e.g., the first body part 21) wearing the ring-shaped wearable device 200 and a neighboring finger (e.g., the second body part 22 and the third body part 23) are attached and spread out, the processor 201 may detect a change of a bending gesture. The processor 201 of the wearable device 200 may identify whether the first motion 611 corresponds to a first gesture G1 belonging to a preset gesture group through the third sensor 330.

For example, referring to FIGS. 6B and 6C, a second motion 612 immediately following the first motion 611 may include moving of the part 20 of the user's body during a change from the state 610b to a state 610c. For example, the processor 201 may detect a change in a gesture of bending and then spreading the finger back again, in a state where a finger (e.g., the first body part 21) wearing a ring-shaped wearable device 200 and a neighboring finger (e.g., the second body part 22 and the third body part 23) are attached and spread out. The processor 201 of the wearable device 200 may receive information related to the second motion 612 through the third sensor 330, based on identifying the first motion 611 corresponding to the first gesture G1. For example, the processor 201 may obtain information related to the moving of the first body part 21 of the user wearing the wearable device 200 and/or inclination of the wearable device according to the moving of the first body part 21, through the third sensor 330. The processor 201 may obtain the second motion 612 and/or information related to the second motion 612, based on at least a portion of the information. For example, the processor 201 may obtain information related to rotation of the first body part 21 and/or moving speed of the first body part 21 of the user wearing the wearable device 200 through the third sensor 330. The processor 201 may obtain the second motion 612 and/or information related to second motion 612, based on at least a portion of the information. However, it is not limited thereto. The processor 201 may be configured to identify whether the second motion 612 corresponds to a second gesture G2 belonging to the preset gesture group, based on receiving the information related to the second motion 612. Based on identifying the second motion 612 corresponding to the second gesture G2, the processor 201 may perform an event for executing a function corresponding to a combination of the first gesture G1 and the second gesture G2 of the external electronic device 101.

For example, while the first motion 611 corresponding to the first gesture G1 and the second motion 612 corresponding to the second gesture G2 immediately following the first motion 611 are performed, the processor 201 may identify whether the wearable device 200 is worn on the user through a first sensor module (e.g., the first sensor module 250 of FIG. 2B). For example, the processor 201 may identify the wearable device 200 worn on the user, based on that at least a portion of light emitted through the light emitter (e.g., the light emitter 251 of FIG. 2B) of the first sensor module 250 and reflected from the first body part 21 of the user wearing the wearable device 200 are received by the light receiver (e.g., the light receiver 252 of FIG. 2B) of the first sensor module 250. The processor 201 may be configured to identify whether the first motion 611 corresponds to the first gesture G1 and whether the second motion 612 corresponds to the second motion 612, through the third sensor 330, based on identifying the wearable device 200 worn on the user. The processor 201 may be configured to bypass identifying the user's motions (the first motion 611 and the second motion 612) through the third sensor 330 while identifying the wearable device 200 separated from the user through the first sensor module 250.

For example, while the first motion 611 corresponding to the first gesture G1 and the second motion 612 corresponding to the second gesture G2 immediately following the first motion 611 are performed, the processor 201 may be configured to identify whether the second body part 22 is positioned in the first groove 311 through the first sensor 321 (or a first electrode (e.g., the first electrode 321a of FIG. 3C) of the first sensor 321) and/or whether the third body part 23 is positioned in the other groove 312 through the second sensor 322 (or a second electrode (e.g., the second electrode 322a of FIG. 3C) of the second sensor 322). The processor 201 may be configured to identify the user's motions (the first motion 611 and the second motion 612) through the third sensor 330, based on identifying the second body part 22 positioned in the first groove 311 and/or the third body part 23 positioned in the second groove 312. The processor 201 may be configured to bypass identifying the user's motions (the first motion 611 and the second motion 612) through the third sensor 330, based on identifying the second body part 22 separated from the first groove 311 and/or the third body part 23 separated from the second groove 312. However, it is not limited thereto. For example, when changing from a state in which the second body part 22 is positioned in the first groove 311 and the third body part 23 is positioned in the second groove 312 to a state in which at least one of the second body part 22 and the third body part 23 is separated from the wearable device 200, the processor 201 may be configured to identify whether the motion corresponds to the preset gesture, based on a user's motion detected through the third sensor 330 within a designated time from the state in which the at least one of the second body part 22 and the third body part 23 is separated from the wearable device 200.

For example, while the first motion 611 corresponding to the first gesture G1 and the second motion 612 corresponding to the second gesture G2 immediately following the first motion 611 are performed, the processor 201 may provide information for unlocking the external electronic device 101 or executing an application through the external electronic device 101 connected to the wearable device 200. For example, while the first motion 611 corresponding to the first gesture G1 and the second motion 612 corresponding to the second gesture G2 immediately following the first motion 611 are performed, the wearable device 200 may be configured to display a screen 620 through the external electronic device 101. The screen 620 may include an image 621 and/or text 622 that provides information for unlocking of the external electronic device 101 or executing an application.

For example, referring to FIG. 6C, when the first motion 611 corresponding to the first gesture G1 and the second motion 612 corresponding to the second gesture G2 immediately following the first motion 611 are completed, the processor 201 may provide information related to execution of a function corresponding to a combination of the first gesture G1 and the second gesture G2 through the external electronic device 101 connected to the wearable device 200. For example, when the first motion 611 corresponding to the first gesture G1 and the second motion 612 corresponding to the second gesture G2 immediately following the first motion 611 are completed, the wearable device 200 may be configured to display a screen 640 through the external electronic device 101. The screen 640 may include an image 641 and/or text 642 indicating that execution of an application of the external electronic device 101 has initiated in response to a combination of the first gesture G1 and the second gesture G2. However, it is not limited thereto.

According to the above-described embodiment, the wearable device 200 may provide various user experiences to the user by causing an event to the external electronic device 101 connected to the wearable device 200 through a motion of the user wearing the wearable device 200.

Figure 7A:
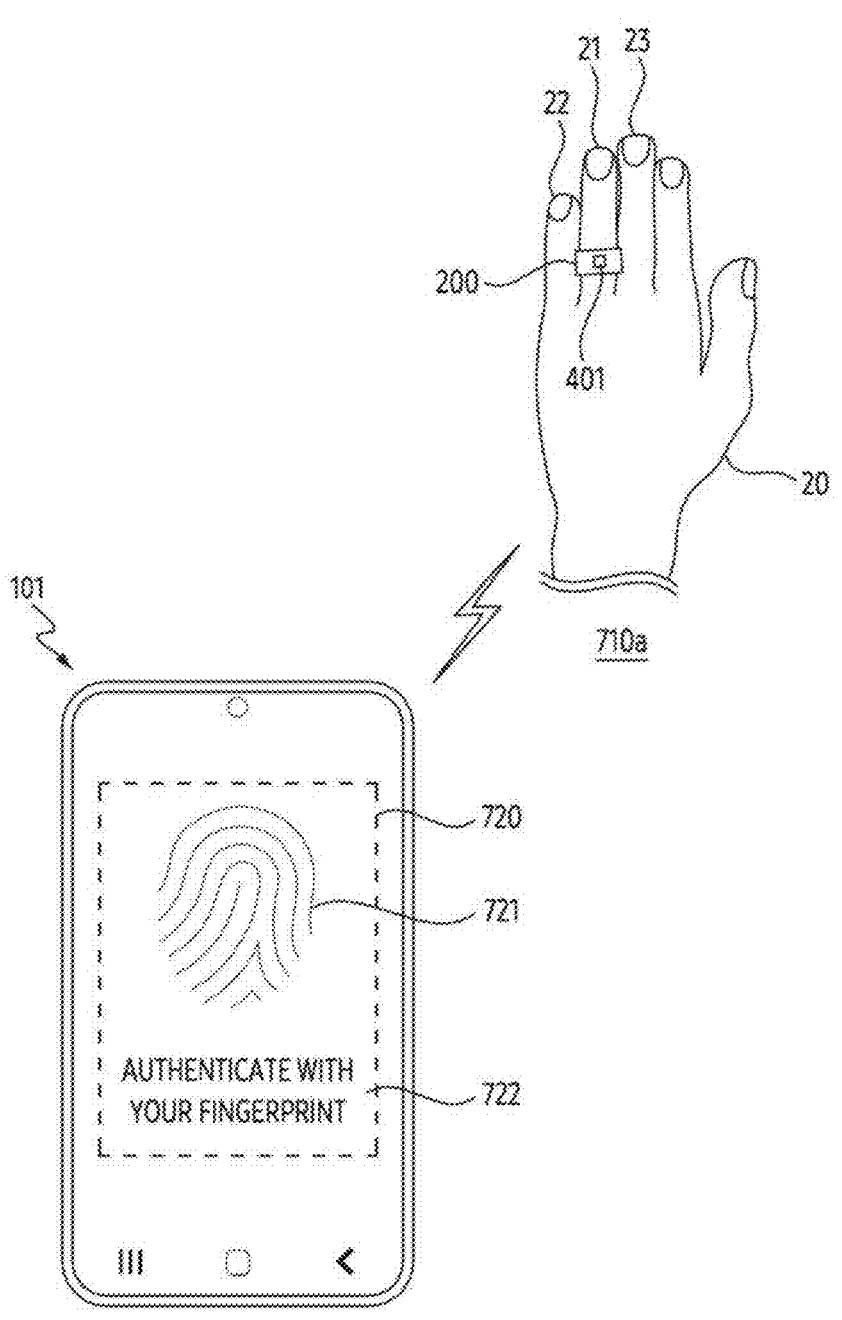
FIGS. 7A and 7B illustrate an exemplary wearable device connected to an external electronic device.
Figure 7B:
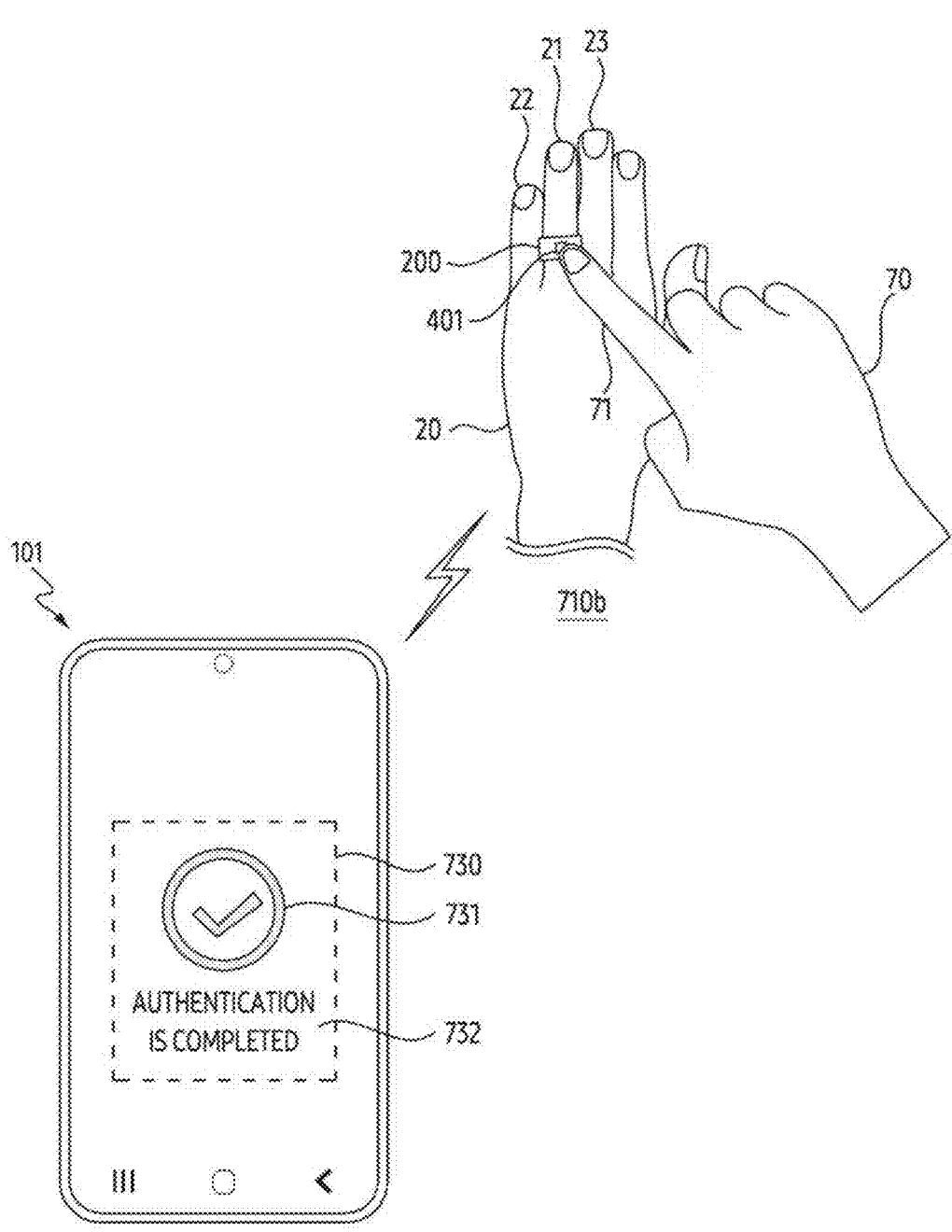

FIGS. 7A and 7B illustrate an exemplary wearable device connected to an external electronic device.

Referring to FIGS. 7A and 7B, a wearable device 200 may be worn on a first body part 21 among a part 20 of a user's body. A housing (e.g., the housing 210 of FIG. 2A) of the wearable device 200 may include a first surface (e.g., the first surface 210a of FIG. 2A) facing the first body part 21 while the wearable device 200 is worn on the first body part 21, a second surface (e.g., the second surface 210b of FIG. 2A) opposite the first surface 210a, and a groove (e.g., the groove 311 of FIG. 3A) formed from the second surface 210b toward the first surface 210a. According to an embodiment, the wearable device 200 may include a first sensor module (e.g., the first sensor module 250 of FIG. 2B) configured to detect biometric information of the user and including a light emitter (e.g., the light emitter 251 of FIG. 2B) facing the first surface 210a and a light receiver (e.g., the light receiver 252 of FIG. 2B) spaced apart from the light emitter 251. According to an embodiment, the housing 210 may include another groove (e.g., the other groove 312 of FIG. 3A) facing the groove 311. The wearable device 200 may include a first sensor (e.g., the first sensor 321 of FIG. 3A) configured to detect a user's second body part 22 distinct from the first body part 21 and positioned in the groove 311. The wearable device 200 may include a second sensor 322 configured to detect a user's third body part 23 distinct from the first body part 21 and the second body part 22 and positioned in the other groove 312. According to an embodiment, the wearable device 200 may include a processor (e.g., the processor 201 of FIG. 2B) and a communication circuit (e.g., the communication circuit 202 of FIG. 2B) for communication with an external electronic device 101.

According to an embodiment, the processor 201 of the wearable device 200 may identify the wearable device 200 worn on the first body part 21 through the first sensor module 250. Based on identifying the wearable device 200 worn on the first body part 21, the processor 201 may drive the first sensor 321 facing the groove 311 and the second sensor 322 facing the other groove 312.

According to an embodiment, the wearable device 200 may include a second sensor module (e.g., the second sensor module 410 of FIG. 4) configured to detect a user's fingerprint, a hole 420 connected to the second sensor module 410 by extending from the second surface 210b of the housing 210 to inside of the housing 210, and at least one cover member 430 disposed on the second sensor module 410 and covering the hole 420. The at least one cover member 430 may be configured to provide a fingerprint authentication region 401 disposed on the second sensor module 410, for fingerprint authentication of the user.

Referring to FIG. 7A, the processor 201 of the wearable device 200 in a state 710a may identify the second body part 22 positioned in the groove 311 through the first sensor 321. The processor 201 may identify the third body part 23 positioned in the other groove 312 through the second sensor 322. For example, the processor 201 may identify a state in which a finger (e.g., the first body part 21) wearing the ring-shaped wearable device 200 and both fingers (e.g., the second body part 22 and the third body part 23) are attached and spread out. The processor 201 may be configured to perform an event for fingerprint authentication of the external electronic device 101 connected to the wearable device 200 through the communication circuit 202, based on identifying the second body part 22 positioned in the groove 311 and the third body part 23 positioned in the other groove 312. The processor 201 of the wearable device 200 may be configured to display a screen 720 indicating information related to fingerprint authentication of the external electronic device 101 through the external electronic device 101. The screen 720 may include an image 721 and/or text 722 related to the user's fingerprint authentication of the external electronic device 101.

Referring to FIG. 7B, the user's fingerprint may be located on the fingerprint authentication region 401 of the wearable device 200 in a state 710b. For example, another part 70 of the user's body that is distinct from the part 20 of the user's body may be disposed on the fingerprint authentication region 401. The second sensor module 410 in the wearable device 200 may detect a fingerprint of a fourth body part 71 located on the fingerprint authentication region 401 among the other part 70 of the body. The processor 201 of the wearable device 200 may be configured to perform the fingerprint authentication on the external electronic device 101 through the communication circuit 202, based on the user's fingerprint identified through the second sensor module 410. For example, the wearable device 200 may be configured to display a screen 730 of the external electronic device 101, based on the user's fingerprint identified through the second sensor module 410. The screen 730 may include an image 731 and/or text 732 indicating that the fingerprint authentication of the external electronic device 101 is completed. However, it is not limited thereto.

According to the above-described embodiment, the wearable device 200 may be configured to cause an event for fingerprint authentication of the user wearing the wearable device 200 on the external electronic device 101, thereby providing various user experiences to the user.

Figure 8B:
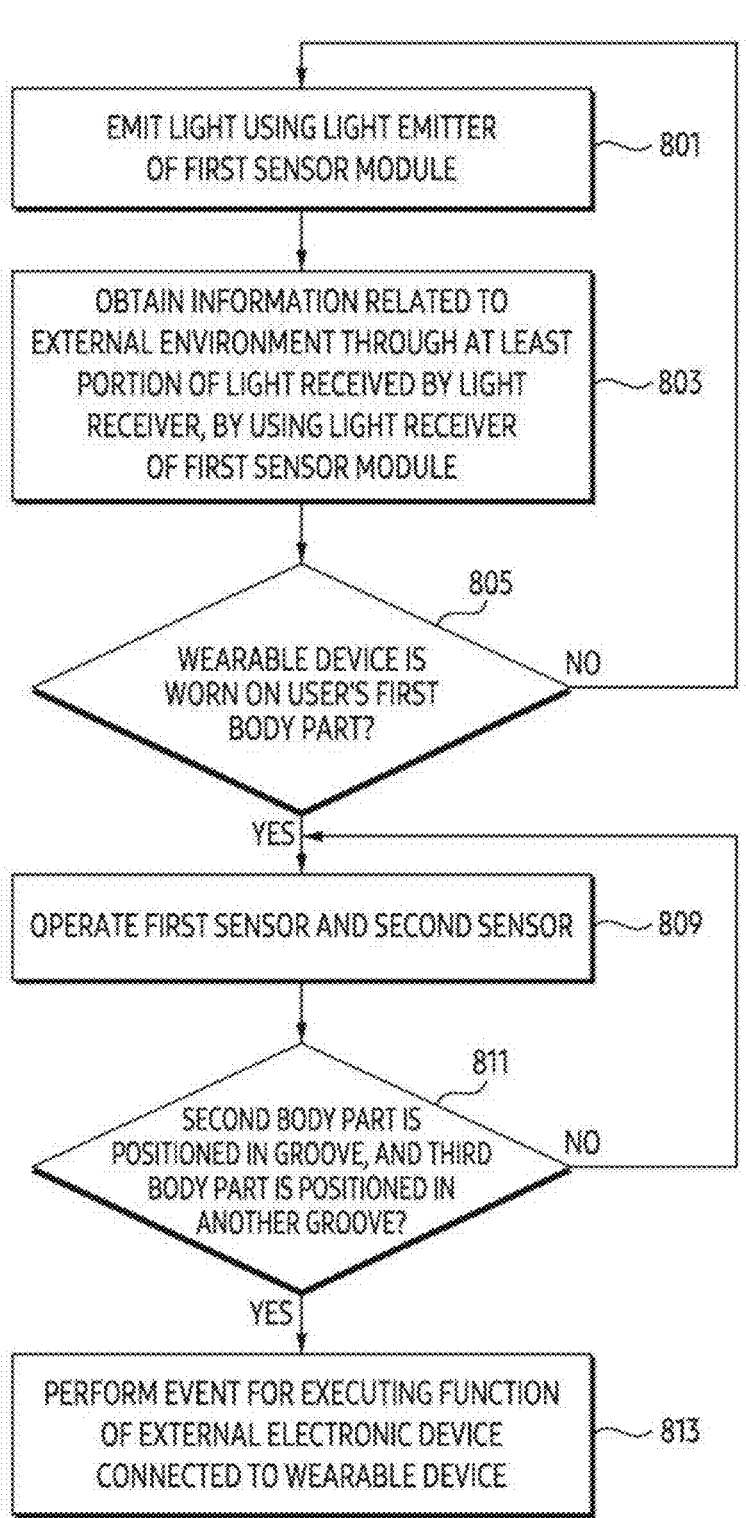

FIGS. 8A and 8B are flowcharts illustrating an operation of a processor of an exemplary wearable device.

An operation of FIGS. 8A and 8B may be performed by the processor 201 of FIG. 2B.

In operation 801, a processor 201 may be configured to emit light using a light emitter (e.g., the light emitter 251 of FIG. 2B) of a first sensor module (e.g., the first sensor module 250 of FIG. 2B). For example, the processor 201 may control the first sensor module 250 so that the light emitter 251 of the first sensor module 250 emits light while the wearable device 200 is turned on.

In operation 803, the processor 201 may be configured to obtain information related to an external environment through at least a portion of light received by a light receiver (e.g., the light receiver 252 of FIG. 2B) of the first sensor module 250 by using the light receiver 252. For example, the light receiver 252 may receive at least a portion of light emitted from the light emitter 251 and reflected by a first body part 21 while the wearable device 200 is worn on a user's first body part (e.g., the first body part 21 of FIG. 2A). The processor 201 may be configured to obtain information related to the user through at least a portion of the light reflected by the first body part 21.

In operation 805, the processor 201 may be configured to identify whether the wearable device 200 is worn on the user's first body part 21. For example, the processor 201 may identify whether the wearable device 200 is worn on the first body part 21 through at least a portion of light received by the light receiver 252 of the first sensor module 250. For example, the processor 201 may identify whether the wearable device 200 is worn on the first body part 21 through a change in intensity of a signal obtained through at least a portion of the light received by the light receiver 252. While identifying that the wearable device 200 is not worn on the user's first body part 21 (e.g., operation 805—NO), the processor 201 may be configured to emit light using the light emitter 251 of the first sensor module 250. For example, the processor 201 may be configured to emit light using the light emitter 251 before the wearable device 200 is worn on the user's first body part 21.

Referring to FIG. 8A, in operation 807, the processor 201 may be configured to operate a first sensor (e.g., the first sensor 321 of FIG. 3A), based on identifying that the wearable device 200 is worn on the user's first body part 21. The processor 201 may be configured to provide information indicating that the wearable device 200 is connected to an external electronic device (e.g., the electronic device 101 of FIG. 1) through the external electronic device 101, based on identifying that the wearable device 200 is worn on the user's first body part 21. For example, the processor 201 may be configured to display a screen (e.g., the screen 520 of FIG. 5) indicating that the wearable device 200 is connected to the external electronic device 101 on the external electronic device 101, through a communication circuit (e.g., the communication circuit 202 of FIG. 2B).

Referring to FIG. 8B, in operation 809, the processor 201 may operate the first sensor 321 and the second sensor (e.g., the second sensor 322 of FIG. 3A) based on identifying that the wearable device 200 is worn on the user's first body part 21.

In operation 811, the processor 201 may be configured to identify whether a user's second body part (e.g., the second body part 22 of FIG. 3B) is positioned in a groove (e.g., the groove 311 of FIG. 3A), and a user's third body part 23 is positioned in another groove (e.g., the other groove 312 of FIG. 3A). For example, the processor 201 may identify whether the second body part 22 is positioned in the groove 311 through the first sensor 321 facing the groove 311. For example, the processor 201 may identify whether the third body part 23 is positioned in the other groove 312 through the second sensor 322 facing the other groove 312. The processor 201 may be configured to operate the first sensor 321 and the second sensor 322, while identifying that the second body part 22 is not positioned in the groove 311 or the third body part 23 is not positioned in the other groove 312 (e.g., operation 811—NO). For example, the processor 201 may be configured to operate the first sensor 321 and the second sensor 322 while identifying that the second body part 22 is positioned in the groove 311 and the third body part 23 is not positioned in the other groove 312. For example, the processor 201 may be configured to operate the first sensor 321 and the second sensor 322 while identifying that the second body part 22 is not positioned in the groove 311 and the third body part 23 is positioned in the other groove 312.

In operation 813, the processor 201 may be configured to perform an event for executing a function of the external electronic device 101 connected to the wearable device 200, based on identifying the second body part 22 positioned in the groove 311 and the third body part 23 positioned in the other groove 312. For example, the processor 201 may be configured to perform an event for executing an application of the external electronic device 101 and/or an event for fingerprint authentication through the external electronic device 101, based on identifying the second body part 22 positioned in the groove 311 and the third body part 23 positioned in the other groove 312.

According to the above-described embodiment, the processor 201 of the wearable device 200 may be configured to identify whether the wearable device 200 is worn on the user through the first sensor module 250. The processor 201 may provide a user with various user experiences through the first sensor 321 and/or the second sensor 322, based on identifying the wearable device 200 worn on the user.

Figure 9A:
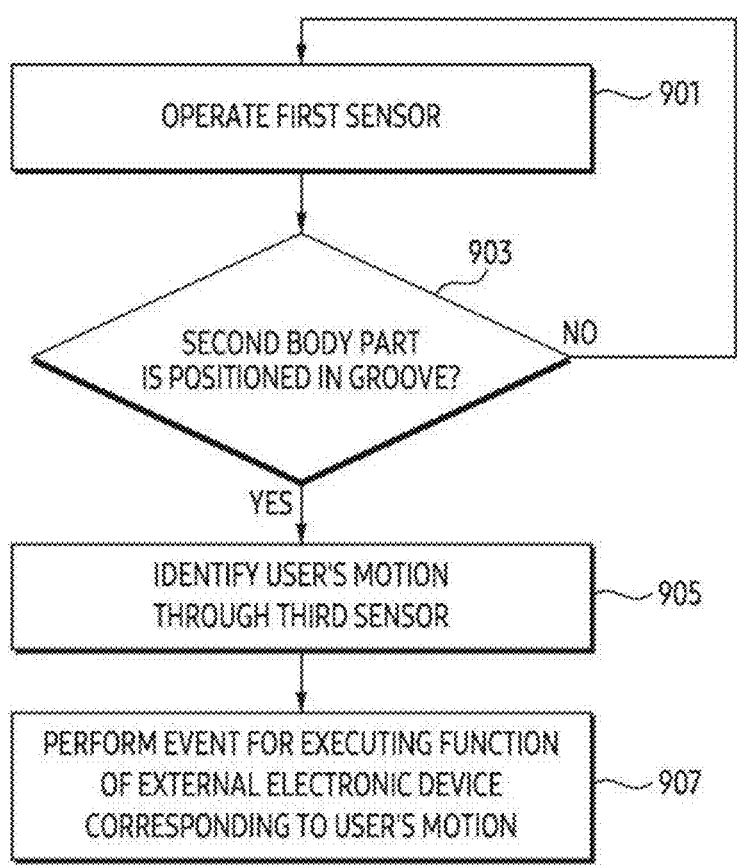
FIGS. 9A and 9B are flowcharts illustrating an operation of a processor of an exemplary wearable device.
Figure 9B:
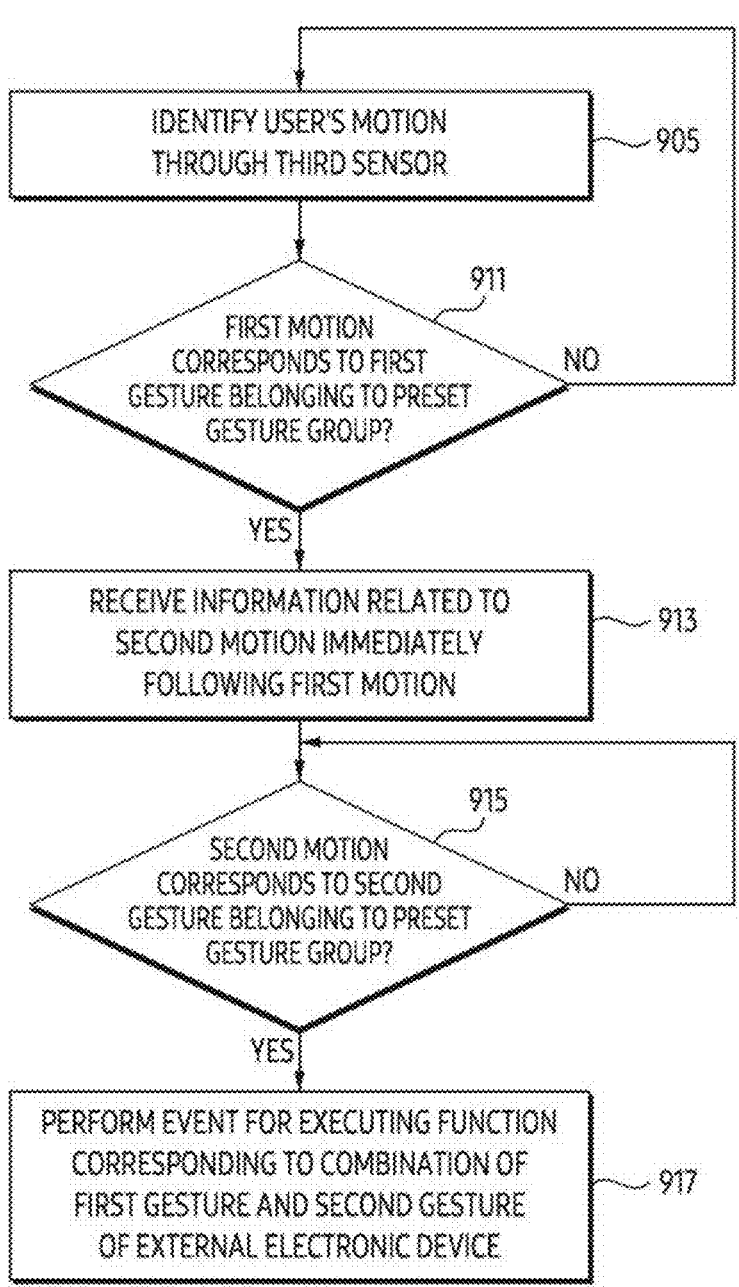

FIGS. 9A and 9B are flowcharts illustrating an operation of a processor of an exemplary wearable device.

FIGS. 9A and 9B may be performed by the processor 201 of FIG. 2B.

Referring to FIG. 9A, in operation 901, the processor 201 may be configured to operate a first sensor (e.g., the first sensor 321 of FIG. 3A). For example, the processor 201 may be configured to supply power to the first sensor 321 through a power management circuit (e.g., the power management circuit 205 of FIG. 2B) and/or a battery (e.g., the battery 230 of FIG. 2B).

In operation 903, the processor 201 may be configured to identify whether a second body part (e.g., the second body part 22 of FIG. 3B) is positioned in a groove (e.g., the groove 311 of FIG. 3A). For example, the processor 201 may be configured to identify whether the second body part 22 is positioned in the groove 311 through the first sensor 321 facing the groove 311. The processor 201 may be configured to operate the first sensor 321 while identifying that the second body part 22 is not positioned in the groove 311 (e.g., operation 903—NO). For example, the processor 201 may be configured to operate the first sensor 321 while the user's second body part 22 is separated from the groove 311.

In operation 905, the processor 201 may be configured to identify a user's motion (e.g., the motion 610 of FIG. 6A) through a third sensor (e.g., the third sensor 330 of FIG. 3C), based on identifying the user's second body part 22 positioned in the groove 311. For example, the third sensor 330 may be configured to detect the user's motion 610 through a first body part (e.g., the first body part 21 of FIG. 2A) of the user on which the wearable device 200 is worn. The processor 201 may be configured to identify the user's motion 610 based on moving of the first body part 21 detected through the third sensor 330. For example, the processor 201 may identify the user's motion 610 based on inclination of the wearable device 200 according to the moving of the first body part 21 detected through the third sensor 330. For example, the processor 201 may identify the user's motion 610, based on rotation of the first body part 21 and/or a moving speed of the first body part 21 detected through the third sensor 330. For example, the processor 201 may identify the user's motion 610, based on a tab or double tab of a finger different from the first body part 21 that may be referred to as the user's finger through the third sensor 330. However, it is not limited thereto.

In operation 907, the processor 201 may be configured to perform an event for executing a function of an external electronic device (e.g., the electronic device 101 of FIG. 1) corresponding to the user's motion 610. For example, the processor 201 may be configured to perform an event for fingerprint authentication of the external electronic device 101 connected to the wearable device 200 and/or application execution, based on the user's motion 610 detected through the third sensor 330. However, it is not limited thereto.

Referring to FIG. 9B, in operation 911, the processor 201 may be configured to identify whether a first motion (e.g., the first motion 611 of FIG. 6A) among the user's motion 610 belongs to a first gesture (e.g., the first gesture G1 of FIG. 6A) belonging to a preset gesture group, based on the user's motion 610 identified through the third sensor 330. The processor 201 may be configured to identify the user's motion 610 through the third sensor 330, while identifying that the first motion 611 does not correspond to the first gesture G1 (e.g., operation 911—NO).

In operation 913, the processor 201 may be configured to receive information related to a second motion (e.g., the second motion 612 of FIG. 6A) of the user immediately following the first motion 611, based on identifying that the first motion 611 corresponds to the first gesture G1. For example, the processor 201 may obtain information related to the second motion 612 through the third sensor 330.

In operation 915, the processor 201 may be configured to identify whether the second motion 612 corresponds to a second gesture (e.g., the second gesture G2 of FIG. 6A) belonging to the preset gesture group based on receiving information related to the second motion 612. The processor 201 may be configured to receive the information related to the second motion 612 through the third sensor 330, while identifying that the second motion 612 does not correspond to the second gesture G2 (e.g., operation 915—NO).

In operation 917, the processor 201 may be configured to perform an event for executing a function corresponding to a combination of the first gesture G1 and the second gesture G2 of the external electronic device 101 connected to the wearable device 200, based on identifying that the second motion 612 corresponds to the second gesture G2. For example, the processor 201 may be configured to execute an application corresponding to a combination of the first gesture G1 and the second gesture G2 of the external electronic device 101 connected to the wearable device 200 and/or perform authenticate, through the external electronic device 101.

According to the above-described embodiment, the processor 201 of the wearable device 200 may provide various user experiences to the user, by causing an event to the external electronic device 101 connected to the wearable device 200 through the motion of the user wearing the wearable device 200.

Figure 10:
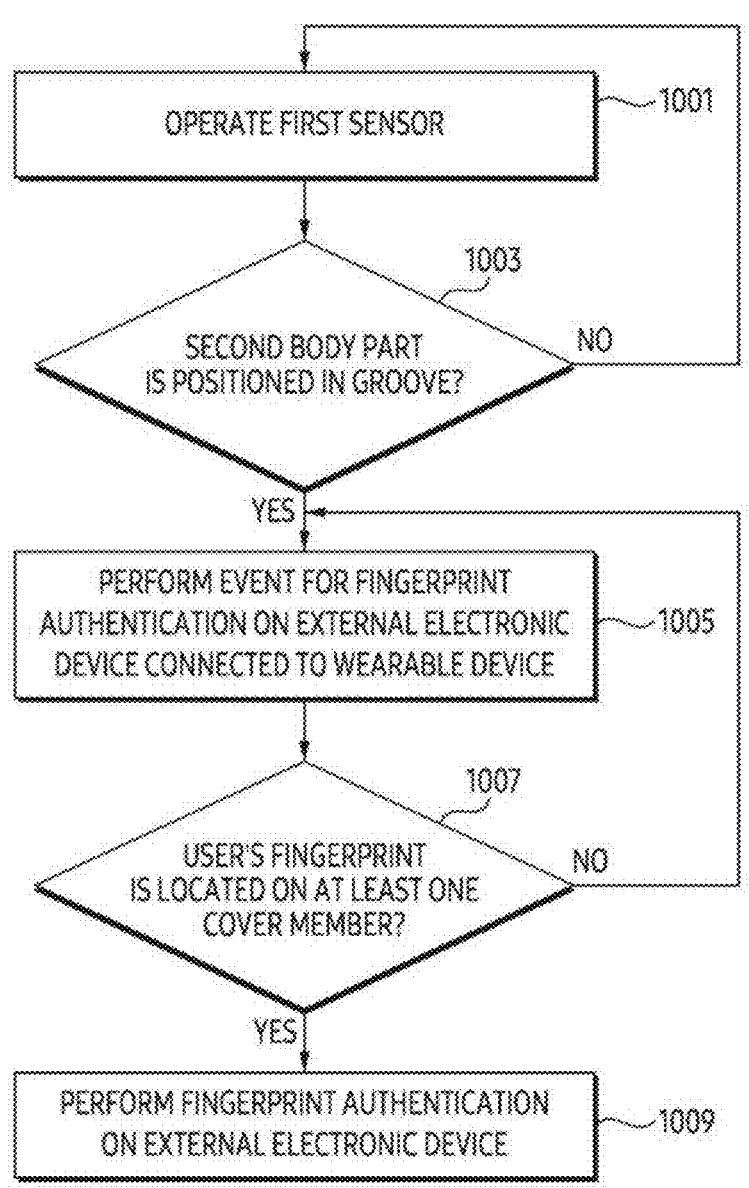
FIG. 10 is a flowchart illustrating an operation of a processor of an exemplary wearable device.

FIG. 10 is a flowchart illustrating an operation of a processor of an exemplary wearable device.

An operation of FIG. 10 may be performed by the processor 201 of FIG. 2B. Operation 1001 and operation 1003 may be an operation corresponding to operation 901 and operation 903 of FIG. 9A, respectively.

In operation 1005, the processor 201 may be configured to perform an event for fingerprint authentication on an external electronic device (e.g., the electronic device 101 of FIG. 1) connected to a wearable device 200, based on identifying a user's second body part (e.g., the second body part 22 of FIG. 3B) positioned in a groove (e.g., the groove 311 of FIG. 3A). For example, the processor 201 may be configured to display a screen (e.g., the screen 720 of FIG. 7A) requesting fingerprint authenticate to the user, through the external electronic device 101, based on identifying the second body part 22 positioned in the groove 311.

In operation 1007, the processor 201 may be configured to identify whether the user's fingerprint is located on at least one cover member (e.g., the at least one cover member 430 of FIG. 4). For example, the processor 201 may be configured to identify whether the user's fingerprint (e.g., the fingerprint of the fourth body part 71 of FIG. 7B) is located on the at least one cover member 430, through a second sensor module (e.g., the second sensor module 410 of FIG. 4) facing the at least one cover member 430. The processor 201 may be configured to perform an event for fingerprint authentication on the external electronic device 101 connected to the wearable device 200 while identifying that the user's fingerprint is not located on the at least one cover member 430 (e.g., operation 1007—NO). For example, the processor 201 may be configured to display a screen (e.g., the screen 720 of FIG. 7A) requesting the user's fingerprint authentication through the external electronic device 101, while identifying that the user's fingerprint (e.g., the fingerprint of the fourth body part 71 of FIG. 7B) is not located on a fingerprint authentication region (e.g., the fingerprint authentication region 401 of FIG. 4) provided by at least one cover member 430.

In operation 1009, the processor 201 may be configured to perform fingerprint authentication on the electronic device 101 connected to the wearable device 200, based on identifying the user's fingerprint located on the at least one cover member 430. For example, the processor 201 may be configured to unlock the external electronic device 101 through the external electronic device 101, based on identifying the user's fingerprint located on the at least one cover member 430. However, it is not limited thereto.

According to the above-described embodiment, the processor 201 of the wearable device 200 may be configured to cause an event for fingerprint authentication of a user wearing the wearable device 200 on the external electronic device 101, thereby providing various user experiences to a user.

The above-described information may be provided as a related art for the purpose of helping to understand the present disclosure. No claim or determination is raised as to whether any of the above-described information may be applied as a prior art related to the present disclosure.

As described above, according to an embodiment, a wearable device (e.g., the electronic device 102 of FIG. 1 and the wearable device 200 of FIG. 2A) may comprise a housing (e.g., the housing 210 of FIG. 2A) including a first surface (e.g., the first surface 210a of FIG. 2A) facing a first body part (e.g., the first body part 21 of FIG. 2A) of a user while the wearable device is worn on the first body part, a second surface (e.g., the second surface 210b of FIG. 2A) opposite to the first surface, and a groove (e.g., the groove 311 of FIG. 3A) formed from the second surface toward the first surface. The wearable device may comprise a first sensor (e.g., the first sensor 321 of FIG. 3A) in the housing disposed toward the groove. The first sensor may be configured to detect a second body part (e.g., the second body part 22 of FIG. 3C) of the user, distinct from the first body part of the user, positioned in the groove. According to the above-described embodiment, the wearable device may provide a user with various user experiences by including the first sensor. By including the groove, the housing may guide the user to a location of the first sensor and increase wearability of the user wearing of the wearable device. The above-described embodiments may have various effects including the effects described above.

According to an embodiment, the groove may include a curved surface (e.g., the curved surface 311a of FIG. 3A) having a curvature to accommodate at least a portion of the second body part by being at least partially bent. According to the above-described embodiment, the wearable device may provide a user with various user experiences by including the first sensor. By including the groove, the housing may guide the user to a location of the first sensor and increase wearability of the user wearing of the wearable device. The above-described embodiments may have various effects including the effects described above.

According to an embodiment, the housing may further include a first frame (e.g., the first frame 211 of FIG. 2A) defining the first surface, and a second frame (e.g., the second frame 212 of FIG. 2A) defining the second surface and coupled to the first frame. The first sensor may be disposed in the second frame. According to the above-described embodiment, the wearable device may provide various user experiences to the user by including the first sensor. By including the groove, the housing may guide the user to a location of the first sensor and increase wearability of the user wearing of the wearable device. The above-described embodiments may have various effects including the effects described above.

According to an embodiment, the first frame may include at least one of silicon, epoxy, and acryl. The second frame may include at least one of metal and titanium. According to the above-described embodiment, the housing may increase the user's wearability on the wearable device, by including the first frame and the second frame including different materials. The above-described embodiments may have various effects including the effects described above.

According to an embodiment, the wearable device may further include a battery (e.g., the battery 230 of FIG. 2B) for charging the wearable device. The wearable device may further include a printed circuit board (e.g., the printed circuit board 240 of FIG. 2B) in the housing that includes a first region (e.g., the first region 241 of FIG. 3A) including at least one electronic component, and a second region (e.g., the second region 242 of FIG. 3A) between the second surface connecting the first region and the battery and the groove. The first sensor may be fastened to the second region. According to the above-described embodiment, the first sensor may provide a user with various user experiences through the groove, by being fastened to the second region. The above-described embodiments may have various effects including the effects described above.

According to an embodiment, a distance (e.g., the d1 of FIG. 3B) between the first surface and the second surface may be greater than a distance (e.g., the d2 of FIG. 3B) between the first surface and the groove. The distance between the first surface and the second surface may be within a range of approximately 2 mm or more and approximately 3 mm or less. A depth of the groove may be within a range of approximately 0.2 mm or more and approximately 1.5 mm or less. According to the above-described embodiment, since the distance between the first surface and the second surface is greater than the distance between the first surface and the groove, the wearable device may provide a user with various user experiences through the groove. The above-described embodiments may have various effects including the effects described above.

According to an embodiment, the wearable device may further include another groove (e.g., the other groove 312 of FIG. 3A) formed from the second surface toward the first surface, and spaced apart from the groove. The wearable device may further comprise a second sensor (e.g., the second sensor 322 of FIG. 3A) in the housing disposed toward the other groove. The second sensor may be configured to detect a third body part (e.g., the third body part 23 of FIG. 3C) of the user, distinct from the first body part and the second body part of the user, positioned in the other groove. According to the above-described embodiment, the wearable device may provide a user with various user experiences together with the groove and the first sensor, by including the other groove and the second sensor. The above-described embodiments may have various effects including the effects described above.

According to an embodiment, the wearable device may further comprise at least one processor (e.g., the processor 201 of FIG. 2B) comprising processing circuitry comprising instructions, a communication circuit (e.g., the communication circuit 202 of FIG. 2B) for communication with an external electronic device (e.g., the electronic device 101 of FIG. 1), and memory (e.g., the memory 203 of FIG. 2B), comprising one or more storage mediums, storing instructions that may be executed by the at least one processor. The instructions, when executed by the at least one processor individually or collectively, may cause the wearable device to identify the second body part positioned in the groove through the first sensor. The instructions, when executed by the at least one processor individually or collectively, may cause the wearable device to identify the third body part positioned in the other groove, through the second sensor. The instructions, when executed by the at least one processor individually or collectively, may cause the wearable device to perform an event for executing a function of the external electronic device connected to the wearable device through the communication circuit based on identifying the second body part positioned in the groove and the third body part positioned in the other groove. According to the above-described embodiment, the processor may be configured to perform an event for executing a function of the external electronic device through the external electronic device, thereby providing a user with various user experiences. The above-described embodiments may have various effects including the effects described above.

According to an embodiment, the wearable device may further comprise a first sensor module (e.g., the first sensor module 250 of FIG. 2B), including a light emitter (e.g., the light emitter 251 of FIG. 2B) configured to emit light toward the first surface and a light receiver (e.g., the light receiver 252 of FIG. 2B) spaced apart from the light emitter, configured to detect biometric information of the user. According to the above-described embodiment, the wearable device may provide a user with various user experiences by including the first sensor module. The above-described embodiments may have various effects including the effects described above.

According to an embodiment, the wearable device may further comprise at least one processor comprising processing circuitry, and memory, comprising one or more storage mediums, storing instructions. The instructions, when executed by the at least one or more processor individually or collectively, may cause the wearable device to emit light using the light emitter of the first sensor circuit. The instructions, when executed by the at least one or more processor individually or collectively, may cause the wearable device to obtain information related to an external environment of the wearable device using the light receiver of the first sensor module through at least a portion of the light received by the light receiver after being emitted from the light emitter. According to the above-described embodiment, the wearable device may provide a user with various user experiences by including the first sensor module. The above-described embodiments may have various effects including the effects described above.

The instructions, when executed by the at least one or more processor individually or collectively, may cause the wearable device to identify whether the wearable device is worn on the first body part of the user through at least a portion of the light received by the light receiver. The instructions, when executed by the at least one or more processor individually or collectively, may cause the wearable device to operate the first sensor based on identifying the wearable device worn on the first body part. According to the above-described embodiment, the wearable device may provide a user with various user experiences by including the first sensor module. The above-described embodiments may have various effects including the effects described above.

According to an embodiment, the wearable device may further comprise a second sensor module (e.g., the second sensor module 410 of FIG. 4), disposed toward the second surface, in the housing configured to detect a fingerprint of the user. The wearable device may further comprise a hole (e.g., the hole 420 of FIG. 4) connected to the second sensor module by extending from the second surface to inside of the housing, and at least one cover member (e.g., the at least one cover member 430 of FIG. 4), disposed on the second sensor module, covering the hole. According to the above-described embodiment, the wearable device may provide a user with various user experiences by including the second sensor module. The above-described embodiments may have various effects including the effects described above.

According to an embodiment, the wearable device may further comprise at least one processor comprising processing circuitry, a communication circuit for communication with an external electronic device, and memory, comprising one or more storage mediums, storing instructions. The instructions, when executed by the at least one or more processor individually or collectively, may cause the wearable device to identify the second body part positioned in the groove through the first sensor. The instructions, when executed by the at least one or more processor individually or collectively, may cause the wearable device to perform an event for fingerprint authentication on the external electronic device connected to the wearable device through the communication circuit based on identifying the second body part positioned in the groove. The instructions, when executed by the at least one or more processor individually or collectively, may cause the wearable device to perform the fingerprint authentication on the external electronic device through the communication circuit based on the fingerprint of the user on the at least one cover member identified through the second sensor module. According to the above-described embodiment, the wearable device may provide a user with various user experiences by including the second sensor module. The above-described embodiments may have various effects including the effects described above.

According to an embodiment, the wearable device may further comprise at least one processor comprising processing circuitry, a communication circuit for communication with an external electronic device, a third sensor (e.g., the third sensor 330 of FIG. 3C) configured to detect a motion (e.g., the motion 610 of FIG. 6A) of the user through the first body part on which the wearable device is worn, memory, comprising one or more storage mediums, storing instructions. The instructions, when executed by the at least one or more processor individually or collectively, may cause the wearable device to identify the second body part positioned in the groove through the first sensor. The instructions, when executed by the at least one or more processor individually or collectively, may cause the wearable device to identify the motion of the user through the third sensor based on identifying the second body part positioned in the groove. The instructions, when executed by the at least one or more processor individually or collectively, may cause the wearable device to perform an event for executing a function of the external electronic device corresponding to the motion of the user through the communication circuit based on the identified motion of the user. According to the above-described embodiment, the wearable device may provide a user with various user experiences by including the third sensor. The above-described embodiments may have various effects including the effects described above.

According to an embodiment, the instructions, when executed by the at least one or more processor individually or collectively, may cause the wearable device to identify whether a first motion (e.g., the first motion 611 of FIG. 6A) among the motion of the user corresponds to a first gesture (e.g., the first gesture G1 of FIG. 6A) belonging to a preset gesture group through the third sensor. The instructions, when executed by the at least one or more processor individually or collectively, may cause the wearable device to receive information related to a second motion (e.g., the second motion 612 of FIG. 6A) immediately following the first motion among the motion of the user through the third sensor based on identifying the first motion corresponding to the first gesture. The instructions, when executed by the at least one or more processor individually or collectively, may cause the wearable device to identify whether the second motion corresponds to a second gesture (e.g., the second gesture G2 of FIG. 6A) belonging to the preset gesture group through the third sensor based on receiving the information related to the second motion. The instructions, when executed by the at least one or more processor individually or collectively, may cause the wearable device to perform an event for executing a function corresponding to a combination of the first gesture and the second gesture of the external electronic device through the communication circuit based on identifying the second motion corresponding to the second gesture. According to the above-described embodiment, the wearable device may provide a user with various user experiences by including the third sensor. The above-described embodiments may have various effects including the effects described above.

According to an embodiment, a wearable device may comprise a housing including a first surface facing a first body part of a user while the wearable device is worn on the first body part, and a second surface opposite to the first surface. The wearable device may comprise a first sensor module, including a light emitter configured to emit light toward the first surface and a light receiver spaced apart from the light emitter, configured to detect biometric information of the user. The wearable device may comprise a second sensor module, disposed toward the second surface, in the housing configured to detect a fingerprint of the user. The wearable device may comprise a hole connected to the second sensor module by extending from the second surface to inside of the housing, and at least one cover member, disposed on the second sensor module, covering the hole. The wearable device may comprise at least one processor comprising processing circuitry, and memory, comprising one or more storage mediums, storing instructions. The instructions, when executed by the at least one or more processor individually or collectively, may cause the wearable device to emit light using the light emitter of the first sensor module. The instructions, when executed by the at least one or more processor individually or collectively, may cause the wearable device to obtain information related to an external environment of the wearable device using the light receiver of the first sensor module through at least a portion of the light received by the light receiver after being emitted from the light emitter. According to the above-described embodiment, the wearable device may provide a user with various user experiences by including the first sensor module and the second sensor module. The above-described embodiments may have various effects including the effects described above.

According to an embodiment, the wearable device may further comprise a first sensor disposed in the housing. The housing may further include a groove formed from the second surface toward the first surface and facing the first sensor. The first sensor may be configured to detect a second body part of the user, distinct from the first body part of the user, positioned in the groove. According to the above-described embodiment, the wearable device may provide a user with various user experiences by including the first sensor. The housing may guide the user to the location of the first sensor and increase the user's wearability on the wearable device, by including the groove. The above-described embodiments may have various effects including the effects described above.

According to an embodiment, the wearable device may further comprise a communication circuit for communication with an external electronic device. The instructions, when executed by the at least one or more processor individually or collectively, may cause the wearable device to identify whether the wearable device is worn on the first body part of the user through at least a portion of the light received by the light receiver. The instructions, when executed by the at least one or more processor individually or collectively, may cause the wearable device to identify the second body part positioned in the groove through the first sensor based on identifying the wearable device worn on the first body part. The instructions, when executed by the at least one or more processor individually or collectively, may cause the wearable device to perform an event for fingerprint authentication on the external electronic device connected to the wearable device through the communication circuit based on identifying the second body part positioned in the groove. The instructions, when executed by the at least one or more processor individually or collectively, may cause the wearable device to perform the fingerprint authentication on the external electronic device through the communication circuit based on the fingerprint of the user on the at least one cover member identified through the second sensor module. According to the above-described embodiment, the wearable device may provide a user with various user experiences by including the first sensor module, the second sensor module, and the first sensor. The above-described embodiments may have various effects including the effects described above.

According to an embodiment, the wearable device may further comprise a third sensor configured to detect a motion of the user through the first body part on which the wearable device is worn. The instructions, when executed by the at least one or more processor individually or collectively, may cause the wearable device to identify the motion of the user through the third sensor based on identifying the second body part positioned in the groove. The instructions, when executed by the at least one or more processor individually or collectively, may cause the wearable device to perform an event for executing a function of the external electronic device corresponding to the motion of the user through the communication circuit based on the identified motion of the user. According to the above-described embodiment, the wearable device may provide a user with various user experiences by including the first sensor module, the second sensor module, the first sensor, and the third sensor. The above-described embodiments may have various effects including the effects described above.

According to an embodiment, the housing may further include a first frame defining the first surface, and a second frame defining the second surface and coupled with the first frame. The first sensor module and the second sensor module may be each disposed in the first frame. According to the above-described embodiment, the housing may increase the user's wearability on the wearable device and provide the user with various user experiences, by including the first frame and the second frame. The above-described embodiments may have various effects including the effects described above.

According to an embodiment, a wearable device to be worn on a finger (e.g., the first body part 21 of FIG. 2A) of a user may comprise a housing, having a ring shape, including an inner wall (e.g., the first frame 211 of FIG. 2A) to contact a portion of the and an outer wall (e.g., the second frame 212 of FIG. 2A) of which a groove is formed on at least a portion. The wearable device may comprise a touch sensor (e.g., the first sensor 321 and the second sensor 322 of FIG. 3A), disposed in the housing, configured to detect a touch on a portion of the groove.

A thickness of the housing at a location on which the groove is formed may be thinner than a thickness of at a remaining location of the housing.

According to an embodiment, while the wearable device is worn on the finger, the groove may have a structure to refrain another finger of the hand adjacent to the finger from being unintendedly detected through the touch sensor, in a state in which a hand including the finger is unfolded.

According to an embodiment, while the wearable device is worn on the finger, the groove may have a curved shaped to accommodate a natural placement of another finger adjacent to the finger of the hand, in a state in which a hand including the finger is gripped.

According to an embodiment, a method of a wearable device may comprise identifying whether the wearable device is worn on a first body part of a user through at least a portion of light received through a light receiver of the electronic device. The method may comprise identifying a second body part of the user, positioned in a groove of the electronic device, through a touch sensor of the electronic device. The method may comprise identifying a motion of the user through a motion sensor of the wearable device, based on identifying the second body part positioned in the groove. The method may comprise identifying whether a first motion among the motion of the user corresponds to a first gesture belonging to a preset gesture group through the motion sensor. The method may comprise receiving information related to a second motion immediately following the first motion through the motion sensor, based on identifying the first motion corresponding to the first gesture. The method may comprise identifying whether the second motion corresponds to a second gesture belonging to the preset gesture group, through the motion sensor, based on receiving the information related to the second motion. The method may comprise performing an event for executing a function corresponding to a combination of the first gesture and the second gesture of an external electronic device through a communication circuit of the wearable device, based on identifying the second motion corresponding to the second gesture.

According to an embodiment, a non-transitory computer readable storage medium storing one or more programs, the one or more programs may comprise instructions which, when executed by at least one processor of a wearable device with a light receiver, a touch sensor, a groove, a motion sensor, and a communication circuit individually or collectively, cause the wearable device to identify whether the wearable device is worn on a first body part of a user through at least a portion of light received through the light receiver. The one or more programs may comprise instructions which, when executed by the at least one processor individually or collectively, cause the wearable to identify a second body part of the user, positioned in the groove of the electronic device through the touch sensor of the electronic device. The one or more programs may comprise instructions which, when executed by the at least one processor individually or collectively, cause the wearable to identify a motion of the user through the motion sensor of the wearable device based on identifying the second body part positioned in the groove. The one or more programs may comprise instructions which, when executed by the at least one processor individually or collectively, cause the wearable to identify whether a first motion among the motion of the user corresponds to a first gesture belonging to a preset gesture group through the motion sensor. The one or more programs may comprise instructions which, when executed by the at least one processor individually or collectively, cause the wearable to receive information related to a second motion immediately following the first motion through the motion sensor, based on identifying the first motion corresponding to the first gesture. The one or more programs may comprise instructions which, when executed by the at least one processor individually or collectively, cause the wearable to identify whether the second motion corresponds to a second gesture belonging to the preset gesture group through the motion sensor, based on receiving the information related to the second motion. The one or more programs may comprise instructions which, when executed by the at least one processor individually or collectively, cause the wearable to perform an event for executing a function corresponding to a combination of the first gesture and the second gesture of an external electronic device through a communication circuit of the wearable device, based on identifying the second motion corresponding to the second gesture.

The effects that can be obtained from the present disclosure are not limited to those described above, and any other effects not mentioned herein will be clearly understood by those having ordinary knowledge in the art to which the present disclosure belongs, from the following description.

The electronic device according to various embodiments may be one of various types of electronic devices. The electronic devices may include, for example, a portable communication device (e.g., a smartphone), a computer device, a portable multimedia device, a portable medical device, a camera, a wearable device, or a home appliance.

According to an embodiment of the disclosure, the electronic devices are not limited to those described above.

It should be appreciated that various embodiments of the present disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. It is to be understood that a singular form of a noun corresponding to an item may include one or more of the things unless the relevant context clearly indicates otherwise. As used herein, each of such phrases as "A or B," "at least one of A and B," "at least one of A or B," "A, B, or C," "at least one of A, B, and C," and "at least one of A, B, or C," may include any one of or all possible combinations of the items enumerated together in a corresponding one of the phrases. As used herein, such terms as "1st" and "2nd," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with," or "connected with" another element (e.g., a second element), it means that the element may be coupled with the other element directly (e.g., wiredly), wirelessly, or via a third element.

As used in connection with various embodiments of the disclosure, the term "module" may include a unit implemented in hardware, software, or firmware, and may interchangeably be used with other terms, for example, "logic," "logic block," "part," or "circuitry". A module may be a single integral component, or a minimum unit or part thereof, adapted to perform one or more functions. For example, according to an embodiment, the module may be implemented in a form of an application-specific integrated circuit (ASIC).

Various embodiments as set forth herein may be implemented as software (e.g., the program 140) including one or more instructions that are stored in a storage medium (e.g., internal memory 136 or external memory 138) that is readable by a machine (e.g., the electronic device 101). For example, a processor (e.g., the processor 120) of the machine (e.g., the electronic device 101) may invoke at least one of the one or more instructions stored in the storage medium, and execute it, with or without using one or more other components under the control of the processor. This allows the machine to be operated to perform at least one function according to the at least one instruction invoked. The one or more instructions may include a code generated by a complier or a code executable by an interpreter. The machine-readable storage medium may be provided in the form of a non-transitory storage medium. Wherein, the term "non-transitory" simply means that the storage medium is a tangible device, and does not include a signal (e.g., an electromagnetic wave), but this term does not differentiate between a case in which data is semi-permanently stored in the storage medium and a case in which the data is temporarily stored in the storage medium.

According to an embodiment, a method according to various embodiments of the disclosure may be included and provided in a computer program product. The computer program product may be traded as a product between a seller and a buyer. The computer program product may be distributed in the form of a machine-readable storage medium (e.g., compact disc read only memory (CD-ROM)), or be distributed (e.g., downloaded or uploaded) online via an application store (e.g., PlayStore™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to various embodiments, each component (e.g., a module or a program) of the above-described components may include a single entity or multiple entities, and some of the multiple entities may be separately disposed in different components. According to various embodiments, one or more of the above-described components may be omitted, or one or more other components may be added. Alternatively or additionally, a plurality of components (e.g., modules or programs) may be integrated into a single component. In such a case, according to various embodiments, the integrated component may still perform one or more functions of each of the plurality of components in the same or similar manner as they are performed by a corresponding one of the plurality of components before the integration. According to various embodiments, operations performed by the module, the program, or another component may be carried out sequentially, in parallel, repeatedly, or heuristically, or one or more of the operations may be executed in a different order or omitted, or one or more other operations may be added.

What is claimed is:

1. A finger-wearable electronic device comprising:
    a ring-shaped housing comprising:
    a ring-shaped inner side contacted with a finger of a user when the finger-wearable electronic device is worn by the user, and
    a ring-shaped outer side opposite to the ring-shaped inner side;
    a first sensor, disposed in the ring-shaped housing, and configured to obtain data regarding a contact on a first portion of the ring-shaped outer side;
    a second sensor, disposed in the ring-shaped housing, and configured to obtain data regarding a contact on a second portion of the ring-shaped outer side spaced apart from the first portion of the ring-shaped outer side; and
    a biometric sensor, disposed in the ring-shaped housing, the biometric sensor comprising:
    at least one light-emitting circuit configured to emit light through at least one light transmittance portion disposed in the ring-shaped inner side, and
    at least one light-receiving circuit configured to receive the light through the at least one light transmittance portion disposed in the ring-shaped inner side,
    wherein the biometric sensor is disposed between the first sensor and the second sensor.

2. The finger-wearable electronic device of claim 1, wherein the ring-shaped housing comprises:
    a first groove portion recessed from the ring-shaped outer side toward the ring-shaped inner side, and
    a second groove portion recessed from the ring-shaped outer side toward the ring-shaped inner side, spaced apart from the first groove portion,
    wherein the first portion of the ring-shaped outer side is positioned in the first groove portion, and
    wherein the second portion of the ring-shaped outer side is positioned in the second groove portion.

3. The finger-wearable electronic device of claim 2, wherein a first distance between the ring-shaped inner side and the ring-shaped outer side is greater than a second distance between the ring-shaped inner side and the first groove portion, wherein the first distance between the ring-shaped inner side and the ring-shaped outer side is greater than a third distance between the ring-shaped inner side and the second groove portion, wherein the first distance between the ring-shaped inner side and the ring-shaped outer side is in a range of about 2 mm to about 3 mm, wherein a first depth of the first groove portion is in a range of about 0.2 mm to about 1.5 mm, and wherein a second depth of the second groove portion is in a range of about 0.2 mm to about 1.5 mm.

4. The finger-wearable electronic device of claim 1, further comprising:

at least one processor comprising processing circuitry;

communication circuitry configured to communicate with an external electronic device; and memory, comprising one or more storage mediums, storing instructions, wherein the instructions, when executed by the at least one processor individually or collectively, cause the finger-wearable electronic device to:

identify a first touch on the first portion of the ring-shaped outer side through the first sensor;

identify a second touch on the second portion of the ring-shaped outer side through the second sensor; and perform an event for executing a function of the external electronic device communicably connected to the finger-wearable electronic device through the communication circuitry based on identifying the first touch on the first portion of the ring-shaped outer side and the second touch on the second portion of the ring-shaped outer side.

5. The finger-wearable electronic device of claim 1, further comprising:

at least one processor comprising processing circuitry; and memory, comprising one or more storage mediums, storing instructions, wherein the instructions, when executed by the at least one processor individually or collectively, cause the finger-wearable electronic device to:

obtain information related to biometrics using the at least one light-receiving circuit of the biometric sensor through at least a portion of the light received by the at least one light-receiving circuit after being emitted from the at least one light-emitting circuit.

6. The finger-wearable electronic device of claim 5, wherein the instructions, when executed by the at least one processor individually or collectively, further cause the finger-wearable electronic device to:

identify whether the finger-wearable electronic device is worn on the finger of the user through at least a portion of the light received by the at least one light-receiving circuit; and operate the first sensor and the second sensor based on identifying that the finger-wearable electronic device is worn on the finger of the user.

7. A finger-wearable electronic device comprising:

a ring-shaped housing comprising:

a ring-shaped inner side contacted by a finger of a user when the finger-wearable electronic device is worn by the user, a ring-shaped outer side opposite to the ring-shaped inner side, and a hole formed in the ring-shaped outer side;

a cover member, disposed in the ring-shaped outer side, and covering the hole;

a fingerprint sensor disposed toward the ring-shaped outer side and connected to the cover member, the fingerprint sensor comprising:

first light-emitting circuitry configured to emit light through the cover member, and first light-receiving circuitry configured to receive the light through the cover member;

a first sensor, disposed in the ring-shaped housing, configured to obtain data regarding a first contact on a first portion of the ring-shaped outer side; and a second sensor, disposed in the ring-shaped housing, configured to obtain data regarding a second contact on a second portion of the ring-shaped outer side spaced apart from the first portion of the ring-shaped outer side;

wherein the fingerprint sensor is disposed between the first sensor and the second sensor.

8. The finger-wearable electronic device of claim 7, further comprising a motion sensor, disposed in the ring-shaped housing, configured to obtain data regarding a motion of the user through the finger on which the finger wearable electronic device is worn.

9. The finger-wearable electronic device of claim 7, wherein the ring-shaped housing comprises:

a first groove portion recessed from the ring-shaped outer side toward the ring-shaped inner side, and a second groove portion recessed from the ring-shaped outer side toward the ring-shaped inner side, spaced apart from the first groove portion, wherein the first portion of the ring-shaped outer side is positioned in the first groove portion, and wherein the second portion of the ring-shaped outer side is positioned in the second groove portion.

10. The finger-wearable electronic device of claim 9, further comprising a biometric sensor disposed in the ring-shaped housing, wherein the biometric sensor comprises:

second light-emitting circuitry configured to emit another light through at least one light transmittance portion disposed in the ring-shaped inner side, and second light-receiving circuitry configured to receive the another light through the at least one light transmittance portion disposed in the ring-shaped inner side.

11. The finger-wearable electronic device of claim 7, further comprising:

at least one processor comprising processing circuitry;

communication circuitry configured to communicate with an external electronic device; and memory, comprising one or more storage mediums, storing instructions, wherein the instructions, when executed by the at least one processor individually or collectively, cause the finger-wearable electronic device to obtain, via the fingerprint sensor, data regarding a fingerprint of the user in accordance with light emitted through the cover member from the first light-emitting circuitry and the light received through the cover member by the first light-receiving circuitry for performing fingerprint authentication for the external electronic device through the communication circuitry.

12. The finger-wearable electronic device of claim 7, further comprising:

at least one processor comprising processing circuitry;

communication circuitry configured to communicate with an external electronic device; and memory, comprising one or more storage mediums, storing instructions that, wherein the instructions, when executed by the at least one processor individually or collectively, cause the finger-wearable electronic device to:

identify a first touch on the first portion of the ring-shaped outer side through the first sensor, identify a second touch on the second portion of the ring-shaped outer side through the second sensor, based on the first touch on the first portion of the ring-shaped outer side being identified via the first sensor and the second touch on the second portion of the ring-shaped outer side being identified via the second sensor, obtain data via the fingerprint sensor for performing fingerprint authentication for the external electronic device connected to the finger-wearable electronic device through the communication circuitry.

13. The finger-wearable electronic device of claim 12, wherein the instructions, when executed by the at least one processor individually or collectively, cause the finger-wearable electronic device to, based on the first touch on the first portion of the ring-shaped outer side being not identified via the first sensor and/or the second touch on the second portion of the ring-shaped outer side being not identified via the second sensor, disable the fingerprint sensor to obtain data.

14. A finger-wearable electronic device comprising:

a ring-shaped housing comprising:

a ring-shaped inner side contacted by a finger of a user, when the finger-wearable electronic device is worn by the user, a ring-shaped outer side opposite to the ring-shaped inner side, and a groove portion recessed from the ring-shaped outer side toward the ring-shaped inner side;

a sensor, disposed in the ring-shaped housing, configured to obtain data regarding a contact on a portion of the ring-shaped outer side, wherein the portion of the ring-shaped outer side is positioned in the groove portion;

a motion sensor configured to obtain data regarding a motion of the user through the finger on which the finger-wearable electronic device is worn;

at least one processor comprising processing circuitry; and memory, comprising one or more storage mediums, storing instructions, wherein the instructions, when executed by the at least one processor individually or collectively, cause the finger-wearable electronic device to:

identify a touch on the portion of the ring-shaped outer side through the sensor; and identify the motion of the user through the motion sensor based on identifying the touch on the portion of the ring-shaped outer side.

15. The finger-wearable electronic device of claim 14, wherein the ring-shaped housing comprises a hole formed in the ring-shaped outer side, wherein the finger-wearable electronic device further comprises:

a cover member, disposed in the ring-shaped outer side and covering the hole; and a fingerprint sensor comprising:

first light-emitting circuitry configured to emit first light through the cover member, and first light-receiving circuitry configured to receive the first light through the cover member, and wherein the fingerprint sensor is disposed toward the ring-shaped outer side and is connected to the cover member.

16. The finger-wearable electronic device of claim 15, further comprising a biometric sensor disposed in the ring-shaped housing, and wherein the biometric sensor comprises:

second light-emitting circuitry configured to emit second light through at least one light transmittance portion disposed in the ring-shaped inner side, and second light-receiving circuitry configured to receive the second light through the at least one light transmittance portion disposed in the ring-shaped inner side.

17. The finger-wearable electronic device of claim 16, further comprising communication circuitry configured to communicate with an external electronic device, wherein the instructions, when executed by the at least one processor individually or collectively, cause the finger-wearable electronic device to perform a first event for executing a first function of the external electronic device corresponding to the motion of the user through the communication circuitry based on the motion of the user identified.

18. The finger-wearable electronic device of claim 17, wherein the instructions, when executed by the at least one processor individually or collectively, further cause the finger-wearable electronic device to:

identify, through the motion sensor, whether a first motion among the motion of the user corresponds to a first gesture belonging to a preset gesture group;

based on identifying the first motion corresponds to the first gesture, receive, through the motion sensor, information related to a second motion following the first motion;

based on receiving the information related to the second motion, identify, through the motion sensor, whether the second motion corresponds to a second gesture belonging to the preset gesture group; and based on identifying the second motion corresponds to the second gesture, perform a second event for executing a second function corresponding to a combination of the first gesture and the second gesture of the external electronic device through the communication circuitry.

19. The finger-wearable electronic device of claim 18, wherein the instructions, when executed by the at least one processor individually or collectively, further cause the finger-wearable electronic device to:

identify whether the finger-wearable electronic device is worn on the finger of the user through at least a portion of the second light received by the second light-receiving circuitry; and operate the sensor based on identifying that the finger-wearable electronic device is worn on the finger of the user.

20. The finger-wearable electronic device of claim 16, further comprising:

communication circuitry configured to communicate with an external electronic device; and wherein the instructions, when executed by the at least one processor individually or collectively, cause the finger-wearable electronic device to, based on a touch on the portion of the ring-shaped outer side being identified via the sensor, obtain data via the fingerprint sensor for performing fingerprint authentication for the external electronic device connected to the finger-wearable electronic device through the communication circuitry.

* * * * *